(12) United States Patent
Penn

(10) Patent No.: US 9,226,978 B2
(45) Date of Patent: *Jan. 5, 2016

(54) METHOD OF TREATING ISCHEMIC DISORDERS

(71) Applicant: The Cleveland Clinic Foundation, Cleveland, OH (US)

(72) Inventor: Marc S. Penn, Beachwood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/536,819

(22) Filed: Nov. 10, 2014

(65) Prior Publication Data

US 2015/0139967 A1 May 21, 2015

Related U.S. Application Data

(63) Continuation of application No. 12/594,026, filed as application No. PCT/US2008/058461 on Mar. 27, 2008, said application No. 12/594,026 is a continuation-in-part of application No. 10/426,712, filed on Apr. 30, 2003, now abandoned.

(60) Provisional application No. 60/921,044, filed on Mar. 30, 2007, provisional application No. 60/405,274, filed on Aug. 22, 2002.

(51) Int. Cl.
| | |
|---|---|
| A61K 48/00 | (2006.01) |
| A61K 38/19 | (2006.01) |
| A61K 38/28 | (2006.01) |
| A61K 35/28 | (2015.01) |

(52) U.S. Cl.
CPC ............. *A61K 48/0075* (2013.01); *A61K 35/28* (2013.01); *A61K 38/195* (2013.01)

(58) Field of Classification Search
CPC .. A61K 48/0075; A61K 35/28; A61K 38/195
See application file for complete search history.

(56) References Cited

U.S. PATENT DOCUMENTS

| | | | |
|---|---|---|---|
| 3,773,919 A | 11/1973 | Boswell et al. | |
| 5,197,985 A | 3/1993 | Caplan et al. | |
| 5,980,887 A | 11/1999 | Isner et al. | |
| 6,100,242 A | 8/2000 | Hammond | |
| 6,121,246 A | 9/2000 | Isner | |
| 6,121,428 A | 9/2000 | Blank et al. | |
| 6,358,697 B2 | 3/2002 | Rothenberg | |
| 6,479,654 B1 | 11/2002 | Baird | |
| 6,676,937 B1 | 1/2004 | Isner et al. | |
| 6,818,210 B2 | 11/2004 | Field | |
| 7,101,708 B1 | 9/2006 | Lapidot et al. | |
| 7,125,856 B1 | 10/2006 | Isner | |
| 7,141,363 B2 | 11/2006 | Poznansky et al. | |
| 7,393,628 B2 | 7/2008 | Wagner et al. | |
| 7,393,830 B2 | 7/2008 | Shingo et al. | |
| 7,396,537 B1 | 7/2008 | Krupnick | |
| 7,396,680 B2 | 7/2008 | Shmelkov et al. | |
| 7,399,740 B2 | 7/2008 | Eisenbach-Schwartz et al. | |
| 7,399,751 B2 | 7/2008 | Kirkpatrick | |
| 7,402,567 B2 | 7/2008 | Chojkier et al. | |
| 7,402,724 B2 | 7/2008 | Conover | |
| 7,405,076 B2 | 7/2008 | Goldman | |
| 7,405,195 B2 | 7/2008 | Chen et al. | |
| 7,662,392 B2 | 2/2010 | Itescu | |
| 7,854,944 B2 | 12/2010 | Mandrusov et al. | |
| 2002/0039993 A1 | 4/2002 | Winchester et al. | |
| 2002/0061587 A1 | 5/2002 | Anversa | |
| 2002/0094327 A1 | 7/2002 | Petersen | |
| 2002/0107195 A1 | 8/2002 | Gupta | |
| 2002/0111290 A1 | 8/2002 | Homey et al. | |
| 2003/0017141 A1 | 1/2003 | Poznansky et al. | |
| 2003/0199464 A1 | 10/2003 | Itescu | |
| 2004/0037811 A1 | 2/2004 | Penn et al. | |
| 2004/0131585 A1 | 7/2004 | Itescu | |
| 2004/0235160 A1 | 11/2004 | Nishikawa et al. | |
| 2004/0258669 A1 | 12/2004 | Dzau et al. | |
| 2004/0258670 A1 | 12/2004 | Laughlin et al. | |
| 2005/0271639 A1 | 12/2005 | Penn et al. | |
| 2006/0105950 A1 | 5/2006 | Losordo | |
| 2006/0166361 A1 | 7/2006 | Seyda | |
| 2006/0182712 A1 | 8/2006 | Penn et al. | |
| 2007/0056595 A1 | 3/2007 | McLachlan | |
| 2007/0173471 A1 | 7/2007 | Losordo | |
| 2007/0224171 A1 | 9/2007 | Penn | |
| 2007/0258943 A1 | 11/2007 | Penn | |
| 2010/0166717 A1 | 7/2010 | Penn | |
| 2010/0272679 A1 | 10/2010 | Penn | |

FOREIGN PATENT DOCUMENTS

| | | |
|---|---|---|
| EP | 1232759 | 8/2002 |
| EP | 1803464 A1 | 7/2007 |
| EP | 1542701 | 7/2012 |
| JP | 2004099471 | 2/2004 |

(Continued)

OTHER PUBLICATIONS

U.S. Appl. No. 13/556,595, filed Jul. 24, 2012, Penn.
U.S. Appl. No. 13/556,639, filed Jul. 24, 2012, Penn.
Askari et al., "Effect of stromal-cell-derived factor 1 on stem-cell homing and tissue regeneration in ischaemic cardiomyopathy", The Lancet, Aug. 30, 2003, 362(9385), 697-703.
Abbott et al., "Stromel cell-derived factor-1alpha plays a critical role in stem cell recruitment to the heart after myocardial infarction but is not sufficient to induce homing in the absence of injury", Circulation, Nov. 23, 2004, 110(21), 3300-3305.
Cui et al, Highly efficient gene transfer into murine liver achieved by intravenous administration of naked Epstein-Barr virus (EBV)-based plasmid vectors, Gene Therapy, 2001, 8, 1508-1513.
Elmadbouh et al., "Ex vivo delivered stromal cell-derived factor-1alpha promotes stem cell homing and induces angiomyogenesis in the infarcted myocardium", Journal of Molecular and Cellular Cardiology, Apr. 2007, 42(4), 792-803.

(Continued)

*Primary Examiner* — Thaian N Ton
(74) *Attorney, Agent, or Firm* — Baker Hostetler LLP

(57) ABSTRACT

Provided are methods of treating ischemic disorders in a subject includes administering stromal cell derived factor-1 (SDF-1) to ischemic tissue of the subject.

6 Claims, 13 Drawing Sheets

(56) References Cited

FOREIGN PATENT DOCUMENTS

| | | |
|---|---|---|
| JP | 2005-534290 | 11/2005 |
| WO | WO 92/08796 | 5/1992 |
| WO | WO 94/28143 | 12/1994 |
| WO | WO 99/20759 A1 | 4/1999 |
| WO | WO 99/45775 | 9/1999 |
| WO | WO 99/45775 A1 | 9/1999 |
| WO | WO 99/50461 A1 | 10/1999 |
| WO | WO 00/15285 A1 | 3/2000 |
| WO | WO 00/19442 A1 | 4/2000 |
| WO | WO 00/50048 A2 | 8/2000 |
| WO | WO 00/60086 A2 | 10/2000 |
| WO | WO 01/94420 | 12/2001 |
| WO | WO 02/09650 | 2/2002 |
| WO | WO 02/091995 A2 | 11/2002 |
| WO | WO 03/014336 | 2/2003 |
| WO | WO 03/059375 | 7/2003 |
| WO | WO 03/090512 | 11/2003 |
| WO | WO 03/105908 | 12/2003 |
| WO | WO 2004/017978 | 3/2004 |
| WO | WO 2004/017987 A2 | 3/2004 |
| WO | WO 2004/093688 | 11/2004 |
| WO | WO 2005/047494 A2 | 5/2005 |
| WO | WO 2006/030887 | 3/2006 |
| WO | WO 2008/121719 | 10/2008 |
| WO | WO 2011/026041 A2 | 3/2011 |
| WO | WO 2012/037083 A2 | 3/2012 |
| WO | WO 2012/094512 | 7/2012 |

OTHER PUBLICATIONS

Ghadge et al, SDF-1a as a therapeutic Stem cell homing factor in myocardial infarction, Pharmacology & Therapeutics, Jan. 2011, 129(1), 97-108.

Hu, Wei-Shau and Pathak, Vinay, "Design of Retroviral Vectors and Helper Cells for Gene Therapy", Pharmacological Reviews, Dec. 2000, 52(4), 493-511.

Jaleel et al., "Stromel cell-derived factor-1 (SDF-1) signalling regulates human placental trophoblast cell survival", Molecular Human Reproduction, Oct. 8, 2004, 10(12), 901-909.

Lataillade et al., "Stromel cell-derived factor 1 regulates primitive hematopoiesis by suppressing apoptosis and by promoting G(0)/G(1) transition in CD34(+) cells: evidence for an autocrine/paracrine mechanism", Blood, Feb. 15, 2002, 99(4), 1117-1129.

Lee et al, Functional Analysis of the Endothelin-1 Gene Promoter, The Journal of Biological Chemistry, Jun. 1990, 265(18), 10446-10450.

Lieber et al, Integrating adenovirus-adeno-associated virus hybrid vectors devoid of all viral genes, Journal of Virology, Nov. 1999, 73(11), 9314-9324.

Miyoshi et al, Development of a Self-Inactivating Lentivirus Vector, Journal of Virology, Oct. 1998, 72(10), 8150-5157.

Perri et al, Replicon Vectors Derived from Sindbis Virus and Semliki Forest Virus That Establish Persistent Replication in Host Cells, Oct. 2000, 74(20), 9802-9807.

Sasaki et al, "Stromel cell-derviced factor-1 (SDF-1) protects deterioration of cardiac function through angiogenesis after acute myocardial infarction (AMI) in mice", circulation Oct. 26, 2004, 110(17), 111, 77th scientific meeting of the American heart association, New Orleans, LA Nov. 7-10, 2004, Abstract.

Shake et al, Mesenchymal Stem Cell Implantation in a Swine Myocardial Infarct Model: Engraftment and Functional Effects, The Annals of Thoracic Surgical , Jun. 2002, 73(6), 1919-1925.

Tang, Mobilizing of haematopoietic stem cells to ischemic myocardium by plasmid mediated stromal-cell-derived factor-1α (SDF-1 α) treatment, Regulatory Peptides, Feb. 15, 2005, 125(1-3), 1-8.

Yamaguchi et al, "Stromal Cell-Derived Factor-1 effects on Ex vivo expanded endothelial Progenitor Cell Recruitment for Ischemic Neovascularization", Circulation, Mar. 11, 2003, 107(9), 1322-1328.

Yano et al., "Stromel cell derived factor-1 (SDF-1)/CXCL12 attenuates diabetes in mice and promotes pancreatic beta-cell survival by activation of the prosurvival kinase Akt", Diabetes, Dec. 2007, 56(12), 2946-2957.

Zhang et al, SDF-1 expression by mesenchymal stem cells results in trophic support of cardiac myocytes after myocardial infarction, The FASEB Journal, Oct. 2007, 21(12), 3197-3207.

Asahara et al, "VEGF contributes to postnatal neovascularization by mobilizing bone marrow-derived endothelial progenitor cells.", EMBO J., Jul. 15, 1999, 18(14), 3964-3972.

Badillo et al, "Lentiviral gene transfer of SDF-1α to wounds improves diabetic wound healing", Jounral of Surgical Research, Nov. 2007, 143(1), 35-42.

Bauman et al, CXC-4 transduced human mesenchymal stem cells (MSCs) migrate in response to SDF-1alpha., blood, 2001, 98(11 Part1), P87a.

Baumgartner et al, "Constitutive expression of phVEGF165 after intramuscular gene transfer promotes collateral vessel development in patients with critical limb ischemia.", Circulation, Mar. 31, 1998, 97(12), 1114-1123.

Cheng et al, Targeted migration of mesenchymal stem cells modified with CXCR4 gene to infarcted myocardium improves cardiac performance. Molecular Therapy, Mar. 16, 2008, 16(3), 571-579, E-publication Feb. 5, 2008.

Daley et al, "Prospects for stem cell-based therapy", Cell, Feb. 22, 2008, 132(4), 544-548.

Deten et al, "Hematopoietic stem cells do not repair the infarcted mouse heart" Cardiovascular Research, Jan. 1, 2005, 6591), 52-63.

Etzion et al, "Influence of embryonic cardiomyocyte transplantation on the progression of heart failure in a rat model of extensive myocardial infarction.", J. Mol. Cell Cardiol., Jul. 2001, 33(7), 1321-1330.

Ewaga et al, "The earliest stages of B cell development require a chemokine stromal cell-derived factor/preB cell growth-stimulating factor", Immunity, Aug. 15, 2001, 15, 323-334.

Freedman et al, "Therapeutic angiogenesis for coronary artery disease.", Annals Internal Medicine, Jan. 1, 2002, 136(1), 54-71.

Gallagher et al, "Diabetic impairments in NO-Mediated endothelial progenitor cell mobilization and homing are reversed by hyperoxia and SDF-1α", The Journal of clinical investigation, May 2007, 117(5), 1249-1259.

Grines et al, "Angiogenic gene therapy (AGENT) trial in patients with stable angina pectoris.", Circulation, Mar. 19, 2002, 105(11), 1291-1297.

Haider et al, "IGF-1-Overexpressing Mesenchymal Stem Cells Accelerate Bone Marrow Stem Cell Mobilization via Paracrine Activation of SDF-1α/CXCR4 Signaling to Promote Myocardial Repair", Circulation Research, Nov. 21, 2008, 103(11), 1300-1398.

Hariawala et al, "VEGF improves myocardial blood flow but produces EDRF-mediated hypotension in porcine hearts.", J. Surg. Res. Jun. 1996, 63(1), 77-82.

Hattori et al, Plasma elevation of stromal cell-derived factor-1 induces mobilization of mature and immature hematopoietic progenitor and stem cells, Blood, Jun. 1, 2001, 97(11), 3354-3360.

Hiasa et al, "Gene transfer of stromal cell-derived factor-1α enhances ischemic vasculogenesis and angiogenesis via vascular endothelial growth factor/endothelial nitric oxide synthase-related pathway", Circulation, May 25, 2004, 1009, 2454-2461.

Holden et al, "Plasticity: Time for a reappraisal?", Science, Jun. 21, 2002, 296(5576), 2126-2129.

Hu et al, "Stromel cell-derived factor-1α confers protection against myocardial ischemia/reperfusion injury", Circulation, Aug. 7, 2007, 116(6), 654-663.

Jackson et al, "Regeneration of ischemic cardiac muscle and vascular endothelium by adult stem cells.", J. Clin. Invest., Jun. 2001, 107(11), 1395-1402.

Jain et al, "Cell therapy attenuates deleterious ventricular remodeling and improves cardiac performance after myocardial infarction.", Circulation, Apr. 10, 2001, 103, 1920-1927.

Jo et al, "Chemotaxis of primitive hematopoietic cells in response to stromal cell-derived factor-1", J.Clin. Invest., Jan. 2000, 105(1), 101-111.

Kahn et al, Overexpression of CXCR4 on human CD34+ progenitors increases their proliferation, migration, and NOD/SCID repopulation, Blood, Apr. 15, 2004, 103(8), 2942-2949.

(56) References Cited

OTHER PUBLICATIONS

Kanki et al, "Identifiecation of targeting peptides for ischemic myocardium by invivo phage display", Journal of Molecular and Cellular Cardiology, Feb. 24, 2011, 50, 841-848.

Kim, Chang H., and Broxmeyer, Hal E., In Vitro behavior of hematopoietic progenitor cells under the influence of chemoattractants: stromal cell-derived factor-1, steel factor, and the bone marrow environment, Blood, Jan. 1, 1998, 91(1), 100-110.

Kitaori et al, Stromal Cell-derived factor 1/CXCR4 signaling is critical for the recruitment of mesenchymal stem cells to the fracture site during skeletal repair in a mouse model Arthritis & Rheumatism, Mar. 2009, 60(3), 813-823.

Koch et al, "Effect of catheter-based transendocardial delivery of stromal cell-derived factor 1α on left ventricular function and perfusion in a porcine model of myocardial infarction", Basic Research in Cardiology, Jan. 2006, 101(1), 69-77.

Kocher et al, "Neovascularization of ischemic myocardium by human bone-marrow-derived angioblasts prevents cardiomyocyte apoptosis, reduces remodeling and improves cardiac function.", Nat. Med. Apr. 2001, 7(4), 430-436.

Koh et al, "Differentiation and long-term survival of C2C12 Myoblast grafts in heart.", J. Clin. Invest., Sep. 1993, 92(3), 1548-1554.

Koh et al, Targeted Expression of transforming growth factor-beta 1 in intracardiac grafts promotes vascular endothelial cell DNA synthesis., J. Clin. Invest., Jan. 1995, 95(1), 114-121.

Konstan et al, "Compacted DNA nanoparticles administered to the nasal mucosa of cystic fibrosis subjects are safe and demonstrate partial to complete cystic fibrosis transmembrane regulator reconstitiution", Human Gene Therapy, Dec. 2004, 15: 1-15.

Kusano et al, "Sonic hedgehog myocardial gene therapy: Tissue repair through transient reconstitution of embryonic signaling", Nature Medicine, Nov. 2005, 11(11), 1197-1204.

Laham et al, "Local perivascular delivery of basic fibroblast growth factor in patients undergoing coronary bypass surgery: Results of a phase I randomized, Double-blind, placebo-controlled trail." Circulation, Nov. 2, 1999, 100(18), 1865-1871.

Lapidot et al, Current understanding of stem cell mobilization: The roles of chemokines, proteolytic enzymes, adhesion molecules, and stromal cells, Experimental Hematology, Sep. 2002, 30(9), 973-981.

Lee et al, "VEDG gene delivery to myocardium: deleterious effects of unregulated expression.", Circulation, Aug. 2000, 102(8), 898-901.

Li et al, "Cardiomyocyte transplantation improves heart function", Ann Thorac. Surg. Sep. 1996, 62(3), 654-660.

Lopez et al, "Hemodynamic effects of intracoronary VEGF delivery: Evidence of tachyphylaxis and No dependence of response.", Am. J. Physiol., Sep. 1997, 273, (3 Pt2), H1317-H1323.

Ma et al, "Impaired B-Lymphopoiesis, Myelopoiesis, and derailed cerebellar neuron migration in CXCR4-and SDF-1-deficient mice", Proc. Natl. Acad. Sci, USA, Aug. 1998, 95(16), 9448-9453.

Matteucci, M.D., and Caruthers, M.H., "Synthesis of Deoxyoligonucleotides on a Polymer Support. Jun. 1981.", J. Am. Chem. Soc., 103(11), 3185-3191.

Menasche et al, "Myoblast transplantation for heart failure.", Lancet, Jan. 27, 2001, 357(9252), 279-280.

Murry et al, Haematopoietic stem cells do not transdifferentiate into cardiac myocytes in myocardial infarcts, Nature, Apr. 8, 2004, 428(6983), 664-668, Epublication Mar. 21, 2004.

Nagasawa et al, "Defects of B-cell lymphopoiesis and Bone-marrow myelopoiesis in mice lacking the CXC Chemokine PBSF/SDF-1.", Nature, Aug. 15, 1996, 382(6952), 635-638.

Nakayama et al, "Vascular endothelial growth factor synergistically enhances bone morphogenetic protein-4-dependent lymphohematopoietic cell generation from embryonic stem cells in vitro.", blood, Apr. 1, 2000, 95(7), 2275-2283.

Norol et al, "Influence of mobilized stem cells on myocardial infarct repair in a nonhuman primate model", Dec. 15, 2003, Blood, 102(13), 4361-4368.

Ohtsuka et al, "Cytokine therapy prevents left ventricular remodeling and dysfunction after myocardial infarction through neovascularization", FASEB, May 2004, 18, 851-853.

Onai et al, Impairment of lymphopoiesis and myelopoiesis in mice reconstituted with bone marrow-hematopoietic progenitor cells expressing SDF-1-intrakine., Blood, Sep. 15, 2000, 96(6), 2074-2080.

Orlic et al, "Bone marrow cells regenerate infarcted myocardium.", Nature, Apr. 5, 2001, 410(6829), 701-705.

Orlic et al, "Mobilized bone marrow cells repair the infarcted heart, improving function and survival", PNAS, Aug. 28, 2001, 98(18), 10344-10349.

Peled et al, "The chemokine SDF-1 activates the integrins LFA-1, VLA-4, and VLA-5 on Immature human CD34(+) cells: role transendothelial/stromal migration and engraftment of NOD/SCID mice". Blood, Jun. 1, 2000, 95(11), 3289-3296.

Penn et al, Autologous cell transplantation for the treatment of damaged myocardium, Progress in cardiovascular diseases, Jul. 2002, 45(1), 21-32.

Penn et al, Role of stem cell homing in myocardial regeneration, international journal of cardiology, Jun. 2004, 95, S23-S25.

Pfeffer et al, "Ventricular remodeling after myocardial infarction. Experimental observations and clinical implications.", Circulation, Apr. 1990, 81(4), 1161-1172.

Quaini et al, "Chimerism of the transplanted heart.", N. Engl. J. Med., Jan. 2002, 346(1), 5-15.

Rabbany et al, "Continuous delivery of stromal cell-derived factor-1 from alginate scaffolds accelerates wound healing", Cell Transplantation, 2010, 19(4), 399-408, E-publication Dec. 8, 2009.

Rosengart et al, "Angiogenesis gene therapy: Phase I assessment of direct intramyocardial administration of an adenovirus vector expressing VEGF121 cDNA to individuals with clinically significant severe coronary artery disease.", Circulation, Aug. 3, 1999, 100(5), 468-474.

Sasaki et al, "Autologous heart cell transplantation into myocardial scar tissue improves heart function.", J. Mol. Cell Cardiol., Mar. 1999, 31(3), 513-522.

Sasaki et al, "Cardiothoracic transplantation. Fetal cell transplantation: A comparison of three cell types.", J. Thorac. Cardiovac. Surg. Oct. 1999, 118(4), 715-725.

Schenk et al, "Monocyte chemotactic protein-3 is a myocardial mesenchymal stem cell homing factor", stem cells, Jan. 2007, 25(1), 245-251, e-publication Oct. 19, 2006.

Schuh et al, "Transplantation of endothelial progenitor cells improves neovascularization and left ventricular function after myocardial infarction in a rat model", Basic Res. Cardiol., Jan. 2008, 103(1), 69-77, Epublication Nov. 12, 2007.

Scorsin et al, "Comparison of the effects of fetal cardiomyocyte and skeletal myoblast transplantation on postinfarction left ventricular function.", J. Thorac. Cardiovasc. Surg., Jun. 2000, 119(6), 1169-1175.

Sundararaman, "Cell-taught gene therapy for the preservation and regeneration of cardiac tissue following chronic heart failure", Thesis, Cleveland State University, Dec. 2010, pp. 1-192.

Simons et al, Pharmacological treatment of coronary artery disease with recombinant fibroblast growth factor-2: double-blind, randomized, controlled clinical trial., Circulation, Feb. 19, 2002, 105(7), 788-793.

Suzuki et al, "Cell transplantation for the treatment of acute myocardial infarction using vascular endothelial growth factor-expressing skeletal myoblasts.", Circulation, Sep. 18, 2001, 104(12 Suppl 1), 1207-1212.

Tachibana et al, The chemokine receptor CXCR4 is essential for vascularization of the gastrointestinal tract., Nature, Jun. 11, 1998, 393(6685), 591-594.

Taylor et al, "Regenerating functional myocardium: Improved performance after skeletal myoblast transplantation.", Nat. Med. Aug. 1998, 4, 929-933.

Tomita et al, "Improved heart function with myogenesis and angiogenesis after autologous porcine bone marrow stromal cell transplantation.", J. Thorac. Cardiovascular Surg. Jun. 2002, 123(6), 1132-1140.

(56) References Cited

OTHER PUBLICATIONS

Topol, "Reperfusion therapy for acute myocardial infarction with fibrinolytic therapy or combination reduced fibrinolytic therapy and platelet glycoprotein IIB/IIIa Inhibition: The Gusto V Randomised Trial.", Lancet, Jun. 16, 2001, 357(9272), 1905-1914.
Udelson et al, "Therapeutic angiogenesis with recombinant fibroblast growth factor-2 improves stress and rest myocardial perfusion abnormalities in patients with severe symptomatic chronic coronary artery disease.", Circulation, Oct. 3, 2000, 102(14), 1605-1610.
Vale et al, "Randomized, single-blind, placebo-controlled pilot study of catheter-based myocardial gene transfer for therapeutic angiogenesis using left ventricular electromechanical mapping in patients with chronic myocardial ischemia.", circulation, May 2001, 103(17), 2138-2143.
Vigna and Naldini, "Lentiviral vectors: excellent tools for experimental gene transfer and promising candidates for gene therapy", J. Gene Med., Sep.-Oct. 2000, 2(5), 308-316.
Wagers et al, "Little Evidence for Developmental plasticity of adult hematopoietic stem cells", Science, Sep. 2002, 297, 2256-2259.
Wright et al, "Hematopoietic stem cells are uniquely selective in their migratory response to chemokines", J. Exp. Med., May 6, 2002, 195(9), 1145-1154.
Yau et al, Enhanced myocardial angiogenesis by gene transfer with transplanted cells., Circulation, Sep. 18, 2001 104(12 Suppl 1), I218-1222.
Yong et al, "Cord blood progenitor cells have greater transendothelial migratory activity and increased responses to SDF-1 and MIP-3beta compared with mobilized adult progenitor cells.", Br. J. Haematol., Nov. 1999, 107(2), 441-449.
Zhang et al, "Over-expression of CXCR4 on mesenchymal stem cells augments myoangiogenesis in the infarcted myocardium", J. Mol. Cell Cardiol., Feb. 2008, 44(2), 281-292, E-publication Dec. 7, 2007.
Zou et al, "Function of the chemokine receptor CXCR4 in haematopoiesis and in cerebellar development.", Jun. 11, 1998, Nature, 393(6685), 595-599.
Ponte et al. The In Vitro Migration Capacity of Human Bone Marrow Mesenchymal Stem Cells: Comparison of Chemokine and Growth Factor Chemotactic Activities. Stem Cells. Jul. 2007;25(7):1737-45.
Otsuru et al. Circulating bone marrow-derived osteoblast progenitor cells are recruited to the bone-forming site by the CXCR4/stromal cell-derived factor-1 pathway. Stem Cells 2008; 26:223-234.
Shirley et al. Systemic recruitment of Osteoblastic Cells in Fracture Healing. J Orthop Res. Sep. 23, 2005 (5), 1013-21.
Zhou et al, "Mesenchymal Stem/Stromal Cells Transfected with Stromal Derived Factor1 for Therapeutic Neovascularization: Enhancement of Cell Recruitment and Entrapment", Sep. 20, 2006, 68, 1268-1271.
Finkemeir C.G. Bone-Grafting and Bone-Graft Substitutes; Journal of Bone Surgery, Mar. 2002, vol. 84, pp. 454-464.
Satija et al. Mesenchymal Stem Cell-Based Therapy: A New Paradigm in Regenerative Medicine, Jul. 2009, Molecular Medicine, vol. 13, pp. 4385-4402.
Patil et al. The AAPS Journal, DNA-based Therapeutics and Dna Delivery Systems: A comprehensive Review, pp. E61-E77, 2005.
Juengst et al., "What next for human gene therapy" BMJ, vol. 326, pp. 1410-1411, Jun. 2003.
Kay et al., "Viral Vectors for Gene Therapy: The Art of Turning Infectious agents into Vehicles of Therapeutics", Nature Publishing Group, vol. 7, No. 1, pp. 33-40, Jan. 2001.
Trent et al. Genetic and Cellular Therapies from Molecular Med: An Introductory Text, pp. 143-173, 2005.
Brunt et al., Stem Cells and Regenerative Medicine—Future Perspectives, J. Physiol. Pharmacol, pp. 327-335, 2012.
Naldini, Ex Vivo Gene Transfer and Correction for Cell-Based Therapies, Nature Reviews Genetics, pp. 301-315, 2011.
Nguyen et al., Methods to Assess Stem Cell Lineage, Fate and Function, Advanced Drug Delivery Reviews 62, pp. 1175-1186, 2010.
Hiasa et al., Gene Transfer of Stromal Cell-Dervied Factor-1 . . . , Circulation, 109: pp. 2454-2461, May 2004.
Burger et al., CXCR4: A Key Receptor in the Crosstalk Between Tumor Cells and their Microevironment, Blood, pp. 1761-1767, Nov. 2005.
Deglurkar et al., Mechanical and Electrical Effects of Cell-Based Gene Therapy for Ischemic Cardiomyopathy are Independent, Human Gene Therapy, pp. 1144-1151, Nov. 2006.

a.

b.

METHOD OF TREATING ISCHEMIC DISORDERS

CROSS-REFERENCE TO RELATED APPLICATIONS

This application is a continuation of U.S. Ser. No. 12/594,026, filed Mar. 1, 2010 (pending), as the U.S. national stage entry of PCT/US0858461, filed Mar. 27, 2008, which claims priority to U.S. Provisional App. No. 60/921,044, filed Mar. 30, 2007. U.S. Ser. No. 12/594,026 is also a continuation-in-part of U.S. Ser. No. 10/426,712, filed Apr. 30, 2003 (abandoned), which claims priority to U.S. Provisional App. No. 60/405,274, filed Aug. 22, 2002. The entire contents of each of the above-referenced applications are incorporated herein by reference.

SEQUENCE LISTING

The instant application contains a Sequence Listing which has been submitted electronically in ASCII format and is hereby incorporated by reference in its entirety. Said ASCII copy, created on Jan. 29, 2015, is named 101521.000102_SL.txt and is 8,414 bytes in size.

FIELD OF THE INVENTION

The present invention relates to compositions and methods of treating disorders associated with ischemia and/or tissue injury.

BACKGROUND OF THE INVENTION

Ischemia is a condition wherein the blood flow completely obstructed or considerably reduced in localized parts of the body, resulting in anoxia, reduced supply of substrates and accumulation of metabolites. Although the extent of ischemia depends on the acuteness of vascular obstruction, its duration, tissue sensitivity to it, and developmental extent of collateral vessels, dysfunction usually occurs in ischemic organs or tissues, and prolonged ischemia results in atrophy, denaturation, apoptosis, and necrosis of affected tissues.

Ischemic cerebrovascular injury development mechanisms are classified into three types, thrombotic, embolic, and hemodynamic. The principal pathological condition for all three types is nevertheless cerebral ischemia, whose severeness and duration define the extent of cerebral tissue injuries. At the site of severe ischemia, nerve and endothelial cell rapidly suffer from irreversible injuries, forming typical infarction nidi due to necrosis. Although the bloodstream moderately declines and functions of neurocytes are suspended in the ischemic penumbra, their survival capacity is not lost and the remaining cerebrovascular system can recover its functions when circulation is resumed via collateral vessels.

In ischemic cardiopathy, which are diseases that affect the coronary artery and cause myocardial ischemia, the extent of ischemic myocardial cell injury proceeds from reversible cell damage to irreversible cell damage with increasing time of the coronary artery obstruction.

SUMMARY OF THE INVENTION

The present invention relates to methods of mitigating cell apoptosis, treating ischemic disorders, and/or treating cell apoptosis associated with the ischemic disorders and/or tissue injury. The ischemic disorder can include a peripheral vascular disorder, a pulmonary embolus, a venous thrombosis, a myocardial infarction, a transient ischemic attack, unstable angina, cerebral vascular ischemia, a reversible ischemic neurological deficit, ischemic kidney disease, or a stroke disorder. The ischemic disorder can also comprise an iatrogenically induced ischemic disorder.

The methods can include locally administering SDF-1 to apoptotic cells that express or upregulate SDF-1 receptors. The apoptotic cells can include cells to be transplanted to a subject being treated and/or apoptotic cells of ischemic tissue being treated. In an aspect of the invention, the SDF-1 receptors can be expressed as a result of cell injury, an ischemic disorder, and/or tissue injury. In another aspect of the invention, the SDF-1 receptor can comprise CXCR4 and/or CXCR7, and the SDF-1 can be administered at an amount effect to mitigate and/or inhibit apoptosis of the cells and/or to increase Akt-phosphorylation of the cells. The SDF-1 can also be locally administered to ischemic tissue at an amount effective to promote angiogensis in the ischemic tissue and/or recruit stem cells expressing CXCR4 and/or CXCR7 to the ischemic tissue.

In an aspect of the invention, the SDF-1 can be locally administered by expressing the SDF-1 from an apoptotic cell, a biocompatible cell delivered to the apoptotic cells or ischemic tissue, or a cell of the ischemic or injured tissue being treated. The SDF-1 can also be expressed from a cell about the periphery of the ischemic tissue. The SDF-1 can be expressed by genetically modifying one of the forgoing cells using at least one of a vector, plasmid DNA, electroporation, and nano-particles to express SDF-1. The SDF-1 can also be expressed from the foregoing cells by administering an agent to the cells that promotes upregulation of SDF-1 from the cells. The SDF-1 can also be locally administered to apoptotic cell or ischemic tissue by providing the SDF-1 in a pharmaceutical composition and delivering the SDF-1 to the tissue being treated.

The present invention also relates to a method of treating ischemic disorders in a subject by administering stromal cell derived factor-1 (SDF-1) to ischemic tissue of the subject in an amount effective to inhibit apoptosis of cells of the tissue in conjunction with administering MCP-3 to the ischemic tissue at amount effective to recruit stem cells an/or progenitor cells to the ischemic tissue.

The SDF-1 can be administered by delivering a pharmaceutical composition comprising SDF-1 to the tissue being treated and/or expressing SDF-1 in the tissue being treated. The SDF-1 can be expressed in the tissue being treated from a cell that is biocompatible with the ischemic tissue being treated. The SDF-1 can also expressed from a cell of the ischemic tissue or a cell about the periphery of the ischemic tissue. The SDF-1 can be expressed from the cell of the tissue being treated by genetically modifying the cell by at least one of a vector, plasmid DNA, electroporation, and nano-particles to express SDF-1.

The MCP-3 can be administered by delivering a pharmaceutical composition comprising MCP-3 to the tissue being treated or expressing MCP-3 in the tissue being treated. The MCP-3 can be expressed in the tissue being treated from a cell that is biocompatible with the ischemic tissue being treated. The MCP-3 can also be expressed from a cell of the ischemic tissue or a cell about the periphery of the ischemic tissue. The MCP-3 can be expressed from the cell of the tissue being treated by genetically modifying the cell by at least one of a vector, plasmid DNA, electroporation, and nano-particles to express MCP-3.

In a further aspect of the invention, the cell expressing the SDF-1 can also express MCP-3. The cell expressing SDF-1 and MCP-3 can be transfected by a bicistronic expression construct expressing SDF-1 and MCP-3.

The present invention further relates to a pharmaceutical composition for treating ischemic disorders. The pharmaceutical composition includes a therapeutically effective amount of SDF-1 and MCP-3. In an aspect of the invention, the pharmaceutical composition can include at least one expression vector to express SDF-1 and MCP-3 from a cell of the ischemic tissue. The at least one vector can include a bicistronic vector comprising DNA for expressing SDF-1 and DNA for expressing MCP-3. In another aspect of the invention, the pharmaceutical composition can include at least one cell biocompatible with the ischemic tissue that expresses SDF-1 and/or MCP-3 in the ischemic tissue when administered to the ischemic tissue.

A further aspect of the invention relates to a method of treating an ischemic disorder of a mammalian subject. In the method, SDF-1 and MCP-3 can be locally administered to the ischemic tissue and/or areas proximate the ischemic tissue. The concentration (or number) of stem cells in the peripheral blood of the ischemic tissue can be increased from the first concentration to a second concentration while SDF-1 and MCP-3 are provided in the ischemic tissue.

In an aspect of the invention, the number of stem cells and/or progenitor cells in the peripheral blood can be increased by injecting stem cells and/or progenitor cells into the peripheral blood and/or arterial or venous infusion of the stem cells into the mammalian subject being treated. One example of a particular type of stem cell that can be injected or infused in accordance with the present invention is an autologous mesenchymal stem cell (MSC). An example of a progenitor cell that can be potentially injected or infused is a autologous, syngeneic, or allogeneic bone marrow derived multipotent adult progenitor cell (MAPC).

BRIEF DESCRIPTION OF THE DRAWINGS

Further features of the present invention will become apparent to those skilled in the art to which the present invention relates from reading the following description of the invention with reference to the accompanying drawings in which.

DETAILED DESCRIPTION

Figure 1:
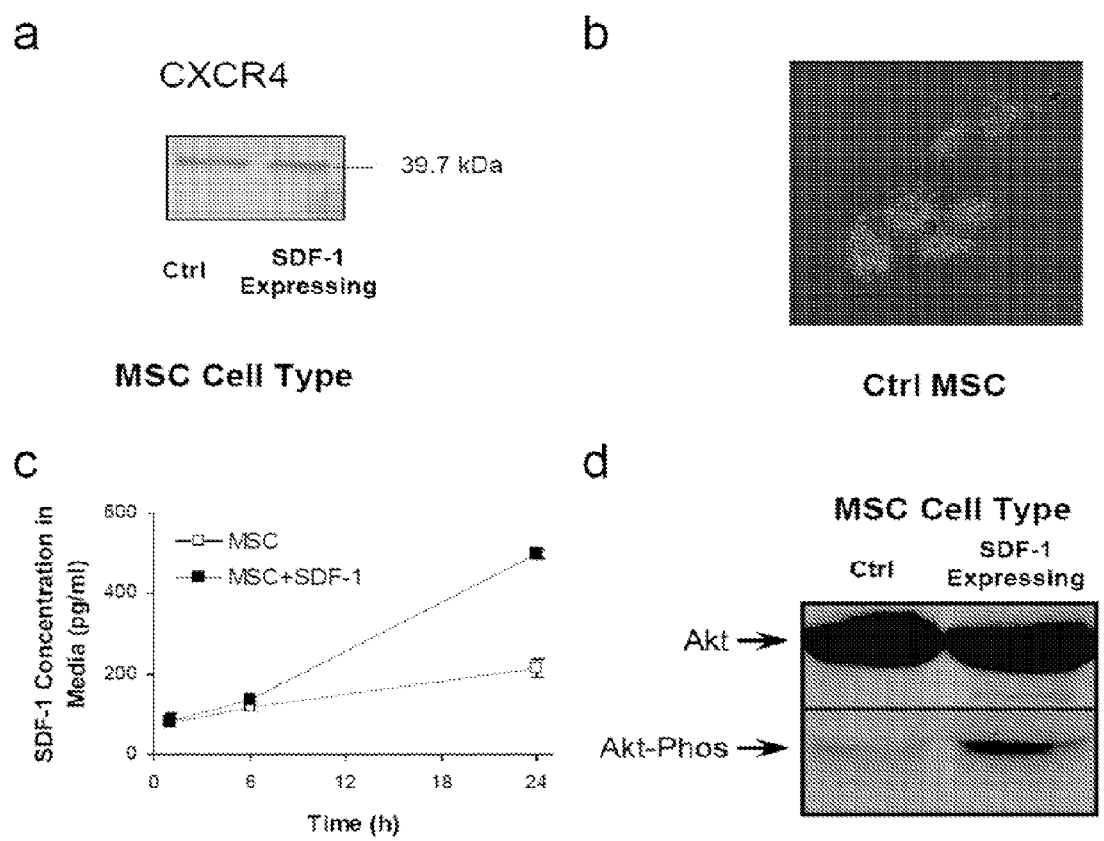
FIG. 1 illustrates a.) Western blot in control and SDF-1 expressing MSC and b.) immunofluorescence staining for CXCR4 in control MSC. c.) Ten thousand control and SDF-1 expressing MSC were separately plated per well in a 12 well plate in serum free DMEM. A 100 μL of media obtained at 1, 6 and 24 h later. SDF-1 levels in the media were quantified using ELISA (R&D Systems). Equal cell number was verified by quantifying total protein per cell layer at the end of the experiment. Data is expressed as picograms of SDF-1 per ml of total media. Experiments were performed in triplicate. Data represent mean±SD. d.) Western blot analysis for Akt and phosphorylated Akt in control and SDF-1 expressing MSC. Western blots were performed with 50 μg of total cell protein separated on a 10% SDS-PAGE gel.

Unless otherwise defined, all technical terms used herein have the same meaning as commonly understood by one of ordinary skill in the art to which this invention belongs. Commonly understood definitions of molecular biology terms can be found in, for example, Rieger et al., Glossary of Genetics: Classical and Molecular, 5th edition, Springer-Verlag: New York, 1991; and Lewin, Genes V, Oxford University Press: New York, 1994.

Methods involving conventional molecular biology techniques are described herein. Such techniques are generally known in the art and are described in detail in methodology treatises, such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described. e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

The present invention relates to methods of mitigating cell apoptosis, treating ischemic disorders, and/or treating cell apoptosis associated with the ischemic disorders and/or tissue injury. The methods can include locally administering (or locally delivering) to apoptotic cells (e.g., endothelial cells, hematopoietic cells, etc.) expressing or upregulating SDF-1 receptors an amount of stromal-cell derived factor-1 (SDF-1) that is effective to mitigate apoptosis of the apoptotic cells. By apoptotic cells it is meant cells that are undergoing apoptosis as a result of the injury or ischemia and/or cells that are at risk of undergoing apoptosis as a result of the injury or ischemia. The SDF-1 receptors can be expressed prior to and/or as a result of cell injury, a ischemic disorder, and/or tissue injury and can include, for example, CXCR4 and/or CXCR7.

It was found that sustained localized administration of SDF-1 to cells expressing SDF-1 receptors or cells with SDF-1 receptors up-regulated as a result of ischemic disorders and/or tissue injury increases Ala phosphorylation in the cells, which can in turn mitigate apoptosis of the cells. Additionally, long-term localized administration of SDF-1 to ischemic tissue facilitates recruitment of stem cells and/or progenitor cells expressing CXCR4 and/or CXCR7 to the tissue being treated, which can facilitate revascularization of the ischemic tissue.

The cell apoptosis in accordance with the present invention can include cell apoptosis that is caused by or results from cell injury, ischemia, or tissue injury as well as cell apoptosis that results from medical procedures, such as cell transplantation, tissue transplantation, and/or cell therapy. Ischemic disorders and/or tissue injuries that result in cell apoptosis and expression or upregulation of SDF-1 receptors and that can be treated by the methods of the present invention can include, for example, a peripheral vascular disorder, a pulmonary embolus, a venous thrombosis, a myocardial infarction, a transient ischemic attack, unstable angina, cerebral vascular ischemia, a reversible ischemic neurological deficit, ischemic kidney disease, or a stroke disorder.

The ischemic disorder can also include an iatrogenically induced ischemic disorder. The iatrogenic ischemic disorder can result from a subject undergoing, for example, angioplasty, heart surgery, lung surgery, spinal surgery, brain surgery, vascular surgery, abdominal surgery, kidney surgery, or organ transplantation surgery. The organ transplantation can comprise heart, lung, pancreas, kidney, or liver translation surgery.

It will be appreciated that the present application is not limited to the preceding ischemic disorders and that other ischemic disorders and tissue injuries, which result in cell apoptosis, can be treated by the compositions and methods of the present invention.

Mammalian subjects, which will be treated by methods and compositions of the present invention, can include any mammal, such as human beings, rats, mice, cats, dogs, goats, sheep, horses, monkeys, apes, rabbits, cattle, etc. The mammalian subject can be in any stage of development including adults, young animals, and neonates. Mammalian subjects can also include those in a fetal stage of development.

In one example, the SDF-1 can be administered to cells of a mammalian tissue undergoing apoptosis as a result of an ischemic disorder and/or tissue injury. It was found that immediately after onset of an ischemic disorder or tissue injury, cells in the ischemic tissue or about the periphery or the border of the ischemic tissue can up regulate expression of SDF-1. After about 24 hours, SDF-1 expression by the cells is reduced. The SDF-1 of the present invention can be administered to the apoptotic cells after about onset of down-regulation of SDF-1 by the cells of the ischemic tissue following tissue injury to about days, weeks, or months after onset of down-regulation of SDF-1. The period of time that the SDF-1 is administered to the cells can comprise from about immediately after onset of the ischemic disorder or tissue injury to about days, weeks, or months after the onset of the ischemic disorder or tissue injury.

In another example, the SDF-1 can be administered to cells or tissue prior to transplantation or administration of the cells or tissue to a subject being treated. Administration of SDF-1 to cells or tissue to be transplanted can potentially mitigate apoptosis of the transplanted cells or tissue and promote long term survival of the cells or tissue. In one aspect of the invention, the SDF-1 can be administered to the cells or tissue to be transplanted by providing the SDF-1 in a culture medium with the cells or tissue. For example, hematopoietic stem cells, mesenchymal stem cells, neural stem cells, other stem cells, and/or other progenitor cells, which express SDF-1 receptors, can be cultured in a medium with SDF-1 prior to transplantation for a therapeutic application. The SDF-1 can promote survival of the cultured stem cells and/or progenitor cells so that the cells have enhanced survivability when administered or transplanted to a subject being treated. In another aspect, the SDF-1 can be co-transplanted with the cells or tissue to be transplanted to mitigate potential apoptosis of the cells or tissue.

SDF-1 in accordance with the present invention can have an amino acid sequence that is substantially similar to a native mammalian SDF-1 amino acid sequence. The amino acid sequence of a number of different mammalian SDF-1 protein are known including human, mouse, and rat. The human and rat SDF-1 amino acid sequences are about 92% identical. SDF-1 can comprise two isoform, SDF-1 alpha and SDF-1 beta, both of which are referred to herein as SDF-1 unless identified otherwise.

SDF-1 can have an amino acid sequence substantially identical to SEQ ID NO: 1. The SDF-1 that is over-expressed can also have an amino acid sequence substantially similar to one of the foregoing mammalian SDF-1 proteins. For example, the SDF-1 that is over-expressed can have an amino acid sequence substantially similar to SEQ ID NO: 2. SEQ ID NO: 2, which substantially comprises SEQ ID NO: 1, is the amino sequence for human SDF-1 and is identified by GenBank Accession No. NP954637. The SDF-1 that is over-expressed can also have an amino acid sequence that is substantially identical to SEQ ID NO: 3. SEQ ID NO: 3, which also substantially comprises SEQ ID NO: 2, includes the amino acid sequences for rat SDF and is identified by GenBank Accession No. AAF01066.

The SDF-1 in accordance with the present invention can also be a variant of mammalian SDF-1, such as a fragment, analog and derivative of mammalian SDF-1. Such variants include, for example, a polypeptide encoded by a naturally occurring allelic variant of native SDF-1 gene (i.e., a naturally occurring nucleic acid that encodes a naturally occurring mammalian SDF-1 polypeptide), a polypeptide encoded by an alternative splice form of a native SDF-1 gene, a polypeptide encoded by a homolog or ortholog of a native SDF-1 gene, and a polypeptide encoded by a non-naturally occurring variant of a native SDF-1 gene.

SDF-1 variants have a peptide sequence that differs from a native SDF-1 polypeptide in one or more amino acids. The peptide sequence of such variants can feature a deletion, addition, or substitution of one or more amino acids of a SDF-1 variant. Amino acid insertions are preferably of about 1 to 4 contiguous amino acids, and deletions are preferably of about 1 to 10 contiguous amino acids. Variant SDF-1 polypeptides substantially maintain a native SDF-1 functional activity. Examples of SDF-1 polypeptide variants can be made by expressing nucleic acid molecules within the invention that feature silent or conservative changes.

SDF-1 polypeptide fragments corresponding to one or more particular motifs and/or domains or to arbitrary sizes, are within the scope of the present invention. Isolated peptidyl portions of SDF-1 can be obtained by screening peptides recombinantly produced from the corresponding fragment of the nucleic acid encoding such peptides. For example, a SDF-1 polypeptides of the present invention may be arbitrarily divided into fragments of desired length with no overlap of the fragments, or preferably divided into overlapping fragments of a desired length. The fragments can be produced recombinantly and tested to identify those peptidyl fragments which can function as agonists of native CXCR-4 polypeptides.

Variants of SDF-1 polypeptides can also include recombinant forms of the SDF-1 polypeptides. Recombinant polypeptides preferred by the present invention, in addition to SDF-1 polypeptides, are encoded by a nucleic acid that can have at least 70% sequence identity with the nucleic acid sequence of a gene encoding a mammalian SDF-1.

SDF-1 variants can include agonistic forms of the protein that constitutively express the functional activities of native SDF-1. Other SDF-1 variants can include those that are resistant to proteolytic cleavage, as for example, due to mutations, which alter protease target sequences. For example, the SDF-1 can include SDF-1 resistant to MMP-2 clevage, such as S-SDF-1(S4V), which is described in Circulation, 2007, 1006. Whether a change in the amino acid sequence of a peptide results in a variant having one or more functional activities of a native SDF-1 can be readily determined by testing the variant for a native SDF-1 functional activity.

The SDF-1 nucleic acid that encodes the SDF-1 protein can be a native or non-native nucleic acid and be in the form of RNA or in the form of DNA (e.g., cDNA, genomic DNA, and synthetic DNA). The DNA can be double-stranded or single-stranded, and if single-stranded may be the coding (sense) strand or non-coding (anti-sense) strand. The nucleic acid coding sequence that encodes SDF-1 may be substantially similar to a nucleotide sequence of the SDF-1 gene, such as nucleotide sequence shown in SEQ ID NO: 4 and SEQ ID NO: 5. SEQ ID NO: 4 and SEQ ID NO: 5 comprise, respectively, the nucleic acid sequences for human SDF-1 and rat SDF-1 and are substantially similar to the nucleic sequences of GenBank Accession No. NM199168 and GenBank Accession No. AF189724. The nucleic acid coding sequence for SDF-1 can also be a different coding sequence which, as a result of the redundancy or degeneracy of the genetic code, encodes the same polypeptide as SEQ ID NO: 1, SEQ ID NO: 2, and SEQ ID NO: 3.

Other nucleic acid molecules that encode SDF-1 within the invention are variants of a native SDF-1, such as those that encode fragments, analogs and derivatives of native SDF-1. Such variants may be, for example, a naturally occurring allelic variant of a native SDF-1 gene, a homolog or ortholog of a native SDF-1 gene, or a non-naturally occurring variant of a native SDF-1 gene. These variants have a nucleotide sequence that differs from a native SDF-1 gene in one or more bases. For example, the nucleotide sequence of such variants can feature a deletion, addition, or substitution of one or more nucleotides of a native SDF-1 gene. Nucleic acid insertions are preferably of about 1 to 10 contiguous nucleotides, and deletions are preferably of about 1 to 10 contiguous nucleotides.

In other applications, variant SDF-1 displaying substantial changes in structure can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide: or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue (e.g., serine or threonine), for (or by) a hydrophobic residue (e.g., leucine, isoleucine, phenylalanine, valine or alanine); (b) a cysteine or proline for (or by) any other residue; (c) a residue having an electropositive side chain (e.g., lysine, arginine, or histidine), for (or by) an electronegative residue (e.g., glutamine or aspartine): or (d) a residue having a bulky side chain (e.g., phenylalanine), for (or by) one not having a side chain, (e.g., glycine).

Naturally occurring allelic variants of a native SDF-1 gene within the invention are nucleic acids isolated from mammalian tissue that have at least 70% sequence identity with a native SDF-1 gene, and encode polypeptides having structural similarity to a native SDF-1 polypeptide. Homologs of a native SDF-1 gene within the invention are nucleic acids isolated from other species that have at least 70% sequence identity with the native gene, and encode polypeptides having structural similarity to a native SDF-1 polypeptide. Public and/or proprietary nucleic acid databases can be searched to identify other nucleic acid molecules having a high percent (e.g., 70% or more) sequence identity to a native SDF-1 gene.

Non-naturally occurring SDF-1 gene variants are nucleic acids that do not occur in nature (e.g., are made by the hand of man), have at least 70% sequence identity with a native SDF-1 gene, and encode polypeptides having structural similarity to a native SDF-1 polypeptide. Examples of non-naturally occurring SDF-1 gene variants are those that encode a fragment of a native SDF-1 protein, those that hybridize to a native SDF-1 gene or a complement of to a native SDF-1 gene under stringent conditions, and those that share at least 65% sequence identity with a native SDF-1 gene or a complement of a native SDF-1 gene.

Nucleic acids encoding fragments of a native SDF-1 gene within the invention are those that encode, amino acid residues of native SDF-1. Shorter oligonucleotides that encode or hybridize with nucleic acids that encode fragments of native SDF-1 can be used as probes, primers, or antisense molecules. Longer polynucleotides that encode or hybridize with nucleic acids that encode fragments of a native SDF-1 can also be used in various aspects of the invention. Nucleic acids encoding fragments of a native SDF-1 can be made by enzymatic digestion (e.g., using a restriction enzyme) or chemical degradation of the full length native SDF-1 gene or variants thereof.

Nucleic acids that hybridize under stringent conditions to one of the foregoing nucleic acids can also be used in the invention. For example, such nucleic acids can be those that hybridize to one of the foregoing nucleic acids under low stringency conditions, moderate stringency conditions, or high stringency conditions are within the invention.

Nucleic acid molecules encoding a SDF-1 fusion protein may also be used in the invention. Such nucleic acids can be made by preparing a construct (e.g., an expression vector) that expresses a SDF-1 fusion protein when introduced into a suitable target cell. For example, such a construct can be made by ligating a first polynucleotide encoding a SDF-1 protein fused in frame with a second polynucleotide encoding another protein such that expression of the construct in a suitable expression system yields a fusion protein.

The nucleic acids encoding SDF-1 can be modified at the base moiety, sugar moiety, or phosphate backbone, for example, to improve stability of the molecule, hybridization, etc. The nucleic acids within the invention may additionally include other appended groups such as peptides (e.g., for targeting target cell receptors in vivo), or agents facilitating transport across the cell membrane, hybridization-triggered cleavage. To this end, the nucleic acids may be conjugated to another molecule, (e.g., a peptide), hybridization triggered cross-linking agent, transport agent, hybridization-triggered cleavage agent, etc.

The SDF-1 can be administered directly to the apoptotic cells or ischemic tissue or about the periphery of apoptotic cells or ischemic tissue to mitigate apoptosis of the cells or tissue. In one aspect of the invention, the SDF-1 can be locally delivered to the apoptotic cells or ischemic tissue neat or in a pharmaceutical composition. In another aspect of the invention, the SDF-1 can be delivered to or about the periphery of the ischemic tissue by administering the SDF-1 neat or in a pharmaceutical composition to or about the ischemic tissue. The pharmaceutical composition can provide localized release of the SDF-1 to the ischemic tissue or cells being treated. Pharmaceutical compositions in accordance with the invention will generally include an amount of SDF-1 or variants thereof admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. Moreover, for human administration, preparations should meet sterility, pyrogenicity, general safety and purity standards as required by FDA Office of Biological Standards.

The pharmaceutical composition can be in a unit dosage injectable form (e.g., solution, suspension, and/or emulsion). Examples of pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol, and the like), suitable mixtures thereof and vegetable oils.

Proper fluidity can be maintained, for example, by the use of a coating, such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various amounts of the other ingredients, as desired.

Pharmaceutical "slow release" capsules or "sustained release" compositions or preparations may be used and are generally applicable. Slow release formulations are generally designed to give a constant drug level over an extended period and may be used to deliver the SDF-1. The slow release formulations are typically implanted in the vicinity of the ischemic tissue site, for example, at the site of cell expressing CXCR4 and/or CXCR7 in or about the ischemic tissue.

Examples of sustained-release preparations include semipermeable matrices of solid hydrophobic polymers containing the SDF-1, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and γ ethyl-L-glutamate; non-degradable ethylene-vinyl acetate; degradable lactic acid-glycolic acid copolymers, such as the LUPRON DEPOT (injectable microspheres composed of lactic acid-glycolic acid copolymer and leuprolide acetate); and poly-D-(−)-3-hydroxybutyric acid.

While polymers such as ethylene-vinyl acetate and lactic acid-glycolic acid enable release of molecules for over 100 days, certain hydrogels release proteins for shorter time periods. When encapsulated SDF-1 remain in the body for a long time, and may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thio-disulfide interchange, stabilization is achieved by modifying sulfhydryl residues, lyophilizing from acidic solutions, controlling moisture content, using appropriate additives, developing specific polymer matrix compositions, and the like.

In certain embodiments, liposomes and/or nanoparticles may also be employed with the SDF-1. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

In another aspect, the SDF-1 can be administered directly to or about the periphery of the ischemic tissue by introducing an agent into target cells that causes, increases, and/or upregulates expression of SDF-1 in or about the periphery of the ischemic tissue. The SDF-1 protein is expressed in or about the periphery of the ischemic tissue can be an expression product of a genetically modified cell. The target cells can include cells within or about the periphery of the ischemic tissue or ex vivo cells that are biocompatible with the ischemic tissue being treated. The biocompatible cells can also include autologous cells that are harvested from the subject being treated and/or biocompatible allogeneic or syngeneic cells, such as autologous, allogeneic, or syngeneic stem cells (e.g., mesenchymal stem cells), progenitor cells (e.g., multipotent adult progenitor cells) and/or other cells that are further differentiated and are biocompatible with the ischemic tissue being treated.

The agent can comprise natural or synthetic nucleic acids, according to present invention and described above, that are incorporated into recombinant nucleic acid constructs, typically DNA constructs, capable of introduction into and replication in the cell. Such a construct preferably includes a replication system and sequences that are capable of transcription and translation of a polypeptide-encoding sequence in a given target cell.

Other agents can also be introduced into the cells to promote expression of SDF-1 from the stem cells. Such agents can include, for example, human Sonic Hedgehog (Shh), human Desert Hedgehog (Dhh), and human Indian Hedgehog (Ihh) proteins, which are described in U.S. Patent Application Publication No. 20060105950 and 20070173471, which are herein incorporated by reference in their entirety. Other examples, agents that increase the transcription of a gene encoding SDF-1, increase the translation of an mRNA encoding SDF-1, and or those that decrease the degradation of an mRNA encoding SDF-1 could be used to increase SDF-1 protein levels. Increasing the rate of transcription from a gene within a cell can be accomplished by introducing an exogenous promoter upstream of the gene encoding SDF-1. Enhancer elements, which facilitate expression of a heterologous gene, may also be employed.

One method of introducing the agent into a target cell involves using gene therapy. Gene therapy refers to gene transfer to express a therapeutic product from a cell in vivo or in vitro. Gene therapy in accordance with the present invention can be used to express SDF-1 protein from a target cell in vivo or in vitro.

In an aspect of the invention, the gene therapy can use naked DNA or a vector including a nucleotide sequence encoding an SDF-1 protein. A "vector" (sometimes referred to as gene delivery or gene transfer "vehicle") refers to a macromolecule or complex of molecules comprising a polynucleotide to be delivered to a target cell, either in vitro or in vivo. The polynucleotide to be delivered may comprise a coding sequence of interest in gene therapy. Vectors include, for example, viral vectors (such as adenoviruses ('Ad'), adeno-associated viruses (AAV), and retroviruses), liposomes and other lipid-containing complexes, and other macromolecular complexes capable of mediating delivery of a polynucleotide to a target cell.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e. positivenegative) markers (see, e.g., Lupton, S., WO 9208796, published May 29, 1992; and Lupton, S., WO 9428143, published Dec. 8, 1994). Such marker genes can provide an added measure of control that can be advantageous in gene therapy contexts. A large variety of such vectors are known in the art and are generally available.

Vectors for use in the present invention include viral vectors, lipid based vectors and other non-viral vectors that are capable of delivering a nucleotide according to the present invention to the target cells. The vector can be a targeted vector, especially a targeted vector that preferentially binds to cells of the ischemic tissue. Viral vectors for use in the invention can include those that exhibit low toxicity to a target cell and induce production of therapeutically useful quantities of SDF-1 protein in a tissue-specific manner.

Examples of viral vectors are those derived from adenovirus (Ad) or adeno-associated virus (AAV). Both human and non-human viral vectors can be used and the recombinant viral vector can be replication-defective in humans. Where the vector is an adenovirus, the vector can comprise a polynucleotide having a promoter operably linked to a gene encoding the SDF-1 protein and is replication-defective in humans.

Other viral vectors that can be use in accordance with the present invention include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid. An example of a HSV vector is one that: (1) is engineered from HSV type I, (2) has its IE genes deleted, and (3) contains a tissue-specific promoter operably linked to a SDF-1 nucleic acid. HSV amplicon vectors may also be useful in various methods of the invention. Typically, HSV amplicon vectors are approximately 15 kb in length, and possess a viral origin of replication and packaging sequences.

Retroviruses, such as C-type retroviruses and lentiviruses, might also be used in the invention. For example, retroviral vectors may be based on murine leukemia virus (MLV). See, e.g., Hu and Pathak, Pharmacol. Rev. 52:493-511, 2000 and Fong et al., Crit. Rev. Ther. Drug Carrier Syst. 17:1-60, 2000. MLV-based vectors may contain up to 8 kb of heterologous (therapeutic) DNA in place of the viral genes. The heterologous DNA may include a tissue-specific promoter and an SDF-1 nucleic acid. In methods of delivery to ischemic tissue, it may also encode a ligand to a tissue specific receptor.

Additional retroviral vectors that might be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells. They are also highly efficient at transducing human epithelial cells.

Lentiviral vectors for use in the invention may be derived from human and non-human (including SIV) lentiviruses. Examples of lentiviral vectors include nucleic acid sequences required for vector propagation as well as a tissue-specific promoter operably linked to a SDF-1 gene. These former may include the viral LTRs, a primer binding site, a polypurine tract, att sites, and an encapsidation site.

A lentiviral vector may be packaged into any suitable lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN), might also be used in the invention. Use of alphaviruses is described in Lundstrom, K., Intervirology 43:247-257, 2000 and Perri et al., Journal of Virology 74:9802-9807, 2000. Alphavirus vectors typically are constructed in a format known as a replicon. A replicon may contain (1) alphavirus genetic elements required for RNA replication, and (2) a heterologous nucleic acid such as one encoding a SDF-1 nucleic acid. Within an alphavirus replicon, the heterologous nucleic acid may be operably linked to a tissue-specific (e.g., myocardium) promoter or enhancer.

Recombinant, replication-defective alphavirus vectors are advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

In many of the viral vectors compatible with methods of the invention, more than one promoter can be included in the vector to allow more than one heterologous gene to be expressed by the vector. Further, the vector can comprise a sequence which encodes a signal peptide or other moiety which facilitates the secretion of a SDF-1 gene product from the target cell.

To combine advantageous properties of two viral vector systems, hybrid viral vectors may be used to deliver a SDF-1 nucleic acid to a target tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Meng et al., Nature Biotechnol. 18:176-186, 2000. Retroviral genomes contained within an adenovirus may integrate within the target cell genome and effect stable SDF-1 gene expression.

Other nucleotide sequence elements which facilitate expression of the SDF-1 gene and cloning of the vector are further contemplated. For example, the presence of enhancers upstream of the promoter or terminators downstream of the coding region, for example, can facilitate expression.

In accordance with another aspect of the present invention, a tissue-specific promoter, can be fused to a SDF-1 gene. By fusing such tissue specific promoter within the adenoviral construct, transgene expression is limited to a particular tissue. The efficacy of gene expression and degree of specificity provided by tissue specific promoters can be determined, using the recombinant adenoviral system of the present invention.

By way of example, the use of tissue specific promoters, such as tissue-specific transcriptional control sequences of left ventricular myosin light chain-2 ($MLC_{2v}$) or myosin heavy chain (MHC), directed to cardiomyocytes alone (i.e., without concomitant expression in endothelial cells, smooth muscle cells, and fibroblasts within the heart) when delivering the SDF-1 gene in vivo provides adequate expression of the SDF-1 protein for therapeutic treatment. Limiting expression to the cardiomyocytes also has advantages regarding the utility of gene transfer for the treatment of CHF. In addition, cardiomyocytes would likely provide the longest transgene expression since the cells do not undergo rapid turnover; expression would not therefore be decreased by cell division and death as would occur with endothelial cells. Endothelial-specific promoters are already available for this purpose (Lee, et al., J. Biol. Chem., 265:10446-10450, 1990).

In addition to viral vector-based methods, non-viral methods may also be used to introduce a SDF-1 nucleic acid into a target cell. A review of non-viral methods of gene delivery is provided in Nishikawa and Huang, Human Gene Ther. 12:861-870, 2001. An example of a non-viral gene delivery method according to the invention employs plasmid DNA to introduce a SDF-1 nucleic acid into a cell. Plasmid-based gene delivery methods are generally known in the art.

Synthetic gene transfer molecules can be designed to form multimolecular aggregates with plasmid DNA. These aggregates can be designed to bind to a target cell. Cationic amphiphiles, including lipopolyamines and cationic lipids, may be used to provide receptor-independent SDF-1 nucleic acid transfer into target cells (e.g., cardiomyocytes). In addition, preformed cationic liposomes or cationic lipids may be mixed with plasmid DNA to generate cell-transfecting complexes. Methods involving cationic lipid formulations are reviewed in Feigner et al., Ann. N.Y. Acad. Sci. 772:126-139, 1995 and Lasic and Templeton, Adv. Drug Delivery Rev. 20:221-266, 1996. For gene delivery, DNA may also be coupled to an amphipathic cationic peptide (Fominaya et al., J. Gene Med. 2:455-464, 2000).

Methods that involve both viral and non-viral based components may be used according to the invention. For example, an Epstein Barr virus (EBV)-based plasmid for therapeutic gene delivery is described in Cui et al., Gene Therapy 8:1508-1513, 2001. Additionally, a method involving a DNA/ligand/ polycationic adjunct coupled to an adenovirus is described in Curiel, D. T., Nat. Immun. 13:141-164, 1994.

Additionally, the SDF-1 nucleic acid can introduced into the target cell by transfecting the target cells using electroporation techniques. Electroporation techniques are well known and can be used to facilitate transfection of cells using plasmid DNA.

Vectors that encode the expression of SDF-1 can be delivered to the target cell in the form of an injectable preparation containing pharmaceutically acceptable carrier, such as saline, as necessary. Other pharmaceutical carriers, formulations and dosages can also be used in accordance with the present invention.

Where the target cell comprises an apoptotic cell, a cell of the ischemic tissue, or about the periphery of the ischemic tissue, the vector can be delivered by direct injection, for example, using a tuberculin syringe under fluoroscopic guidance, at an amount sufficient for the SDF-1 protein to be expressed to a degree which allows for highly effective therapy. By injecting the vector directly to, into, or about the apoptotic cell or the periphery of the ischemic tissue, it is possible to target the vector transfection rather effectively, and to minimize loss of the recombinant vectors.

This type of injection enables local transfection of a desired number of cells, especially in or about the ischemic tissue, thereby maximizing therapeutic efficacy of gene transfer, and minimizing the possibility of an inflammatory response to viral proteins. Optionally, the vector can be administered to the ischemic tissue by attaching a tissue specific cell targeting moiety to the vector and introducing systemically (e.g., intravenous infusion) the tissue specific targeted vector into the subject. Upon introduction into the subject, the tissue specific targeted expression will localize to the targeted tissue and facilitate localized expression of the SDF-1 from the targeted tissue.

Where the target cell is a cultured cell that is later transplanted into ischemic tissue, the vectors can be delivered by direct injection into the culture medium. A SDF-1 nucleic acid transfected into cells may be operably linked to a regulatory sequence.

The transfected target cells can then be transplanted to a subject or to the ischemic tissue by well known transplantation techniques, such as by direct injection. By first transfecting the target cells in vitro and then transplanting the transfected target cells to the ischemic tissue, the possibility of inflammatory response in the ischemic tissue is minimized compared to direct injection of the vector into the ischemic tissue. Optionally, the transfected cells can be administered to the ischemic tissue by attaching a tissue specific cell targeting moiety to the transfected cells and introducing the cells systemically (e.g., intravenous infusion) into the subject. Upon introduction into the subject, the tissue specific targeted cells will localize to the targeted tissue and facilitate localized expression of the SDF-1 from the targeted tissue.

SDF-1 can be expressed for any suitable length of time within the target cell, including transient expression and stable, long-term expression. In one aspect of the invention, the SDF-1 nucleic acid will be expressed in therapeutic amounts for a defined length of time effective to mitigate apoptosis of the apoptotic cells.

A therapeutic amount is an amount, which is capable of producing a medically desirable result in a treated animal or human. As is well known in the medical arts, dosage for any one animal or human depends on many factors, including the subject's size, body surface area, age, the particular composition to be administered, sex, time and route of administration, general health, and other drugs being administered concurrently. Specific dosages of proteins, nucleic acids, or small molecules) can be determined readily determined by one skilled in the art using the experimental methods described below.

Long term SDF-1 expression is advantageous because it allows the concentration of stem cells to be increased in the ischemic tissue. Chronic up-regulation in SDF-1 protein expression causes long term homing of stem cells into the ischemic tissue from the peripheral blood without the need of stem cell mobilization.

Another aspect of the invention relates to a method of treating ischemic disorders in a subject by administering monocyte chemotactic protein-3 (MCP-3) to the ischemic tissue at amount effective to recruit stem cells an/or progenitor cells to the ischemic tissue in conjunction with the administering SDF-1 to ischemic tissue described above to inhibit apoptosis of cells of the tissue.

The MCP-3 in accordance with the present invention can be administered to or about the ischemic tissue of a mammalian subject to induce mobilization of stem cells and/or progenitor cells of the subject to the tissue for therapeutic applications and/or cellular therapy. The of stem cells and/or progenitor cells, which are induced, can differentiate into specialized and/or partially specialized cells that can repopulate (i.e., engraft), revascularize, and partially or wholly restore the normal function of the tissue being treated.

Stem cells in accordance with the present invention include unspecialized autologous, syngeneic, or allogeneic cells that can self-renew indefinitely and that can differentiate into more mature cells with specialized functions. In humans, stem cells have been identified in the inner cell mass of the early embryo, in some tissues of the fetus, the umbilical cord and placenta, and in several adult organs. In some adult organs, stem cells can give rise to more than one specialized cell type within that organ. Stem cells, which are able to differentiate into cell types beyond those of which they normally reside exhibit plasticity. When a stem cell is found to give rise to multiple tissue types associated with different organs it is referred to as multipotent or pluripotent.

One example of a particular type of stein cell that can be induced by the MCP-3 in accordance with the present invention is a mesenchymal stem cell (MSC). MSCs include the formative pluripotent blast or embryonic cells that differentiate into the specific types of connective tissues, (i.e., the tissue of the body that support specialized elements, particularly including adipose, osseous, cartilaginous, elastic, muscular, and fibrous connective tissues depending on various in vivo or in vitro environmental influences. These cells can be present in bone marrow, blood, dermis, and periosteum and can be isolated and purified using various well known methods, such as those methods disclosed in U.S. Pat. No. 5,197, 985 to Caplan and Haynesworth, herein incorporated by reference, as well as other numerous literature references.

An example of a progenitor cell that can be potentially induced by MCP-3 in accordance with the presence is a multipotent adult progenitor cell (MAPC) (e.g., skeletal derived MAPC). MAPCs in accordance with the present invention comprise adult progenitor or stem cells that are capable of differentiating into cells types beyond those of the tissues in which they normally reside (i.e., exhibit plasticity). Examples of MAPCs can include adult MSCs and hematopoietic progenitor cells. Sources of MAPCs can include bone marrow, blood, ocular tissue, dermis. liver, and skeletal muscle. By way of example, MAPCs comprising hematopoietic progenitor cells can be isolated and purified using the methods disclosed in U.S. Pat. No. 5,061,620, herein incorporated by reference, as well as other numerous literature sources.

Stems cells, such as MSCs, MAPCs, and/or other stem cells, can naturally express various CXC and CC chemokine receptors, including CXCR5, CCR-1, Cmkbr1L2, CCR2, CCR3, CCR5, CCR7, CCR8, CCR9, CMKOR1, and CX3CR1. It was found that MCP-3 can function as chemoattractants for MSCs and/or MAPCs in a mammalian subject.

The MCP-3 in accordance with the present invention can have amino sequence substantially similar to native mammalian MCP-3. For example, the MCP-3 can have amino sequences substantially similar to, respectively, SEQ ID NO: 6, which is substantially similar to the nucleic sequences of, respectively, GenBank Accession No. CAA50407.

The MCP-3 of the present invention can also be a variant of native MCP-3, such as a fragment, analog and derivative of mammalian MCP-3. Such variants can include, for example, a polypeptide encoded by a naturally occurring allelic variant of a native MCP-3 gene (i.e., a naturally occurring nucleic acid that encodes a naturally occurring mammalian MCP-3), a polypeptide encoded by an alternative splice form of a native MCP-3 gene, a polypeptide encoded by a homolog or ortholog of a native MCP-3 gene, and a polypeptide encoded by a non-naturally occurring variant of a native MCP-3 gene.

MCP-3 variants can have a peptide (or amino acid) sequence that differs from native MCP-3 in one or more amino acids. The peptide sequence of such variants can feature a deletion, addition, or substitution of one or more amino acids of MCP-3 protein. Amino acid insertions are preferably of about 1 to 4 contiguous amino acids, and deletions are preferably of about 1 to 10 contiguous amino acids. Variant MCP-3 proteins substantially maintain a native MCP-3 protein functional activity. Examples of MCP-3 protein variants can be made by expressing nucleic acid molecules within the invention that feature silent or conservative changes.

MCP-3 protein fragments corresponding to one or more particular motifs and/or domains or to arbitrary sizes, are within the scope of the present invention. Isolated peptidyl portions of MCP-3 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a MCP-3 protein of the present invention may be arbitrarily divided into fragments of desired length with no overlap of the fragments, or preferably divided into overlapping fragments of a desired length. The fragments can be produced recombinantly and tested to identify those peptidyl fragments which can function as agonists of a native MCP-3 protein.

Variants of MCP-3 protein can also include recombinant forms of the proteins. Recombinant polypeptides preferred by the present invention, in addition to a MCP-3 protein, are encoded by a nucleic acid that can have at least 85% sequence identity with the nucleic acid sequence of a gene encoding a mammalian protein.

MCP-3 protein variants can include agonistic forms of the protein that constitutively express the functional activities of a native MCP-3 protein. Other protein variants can include those that are resistant to proteolytic cleavage, as for example, due to mutations, which alter protease target sequences. Whether a change in the amino acid sequence of a peptide results in a variant having one or more functional activities of a native MCP-3 protein can be readily determined by testing the variant for a native MCP-3 protein functional activity.

Nucleic acid molecules that encode the MCP-3 protein can be a native or non-native nucleic acid and be in the form of RNA or in the form of DNA (e.g., cDNA, genomic DNA, and synthetic DNA). The DNA can be double-stranded or single-stranded, and if single-stranded may be the coding (sense) strand or non-coding (anti-sense) strand.

For example, nucleic acid molecules that encode the MCP-3 can have sequences substantially similar to, respectively, SEQ ID NO: 7. SEQ ID NO: 7 is substantially similar to the nucleic sequences of GenBank Accession No. NM006273.

Other nucleic acid molecules that encode MCP-3 protein within the invention can be variants of a native MCP-3 protein gene, such as those that encode fragments, analogs and derivatives of a native MCP-3 protein. Such variants may be, for example, a naturally occurring allelic variant of a native MCP-3 gene, a homolog of a native MCP-3 gene, or a non-naturally occurring variant of a native MCP-3 gene. These variants have a nucleotide sequence that differs from a native MCP-3 gene in one or more bases. For example, the nucleotide sequence of such variants can feature a deletion, addition, or substitution of one or more nucleotides of a native MCP-3 gene. Nucleic acid insertions are preferably of about 1 to 10 contiguous nucleotides, and deletions are preferably of about 1 to 10 contiguous nucleotides.

In other applications, variant native MCP-3 proteins displaying substantial changes in structure can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histidine, for (or by) an electronegative residue, e.g., glutamine or aspartine; or (d) a residue having a bulky side chain, e.g., phenylalanine, for (or by) one not having a side chain, e.g., glycine.

Naturally occurring allelic variants of a native MCP-3 gene within the invention are nucleic acids isolated from mammalian tissue that have at least 75% sequence identity with a native MCP-3 gene, and encode polypeptides having structural similarity to a native MCP-3, protein. Homologs or orthologs of a native MCP-3 gene within the invention are nucleic acids isolated from other species that have at least 75% sequence identity with the native gene, and encode polypeptides having structural similarity to a native MCP-3 protein. Public and/or proprietary nucleic acid databases can be searched to identify other nucleic acid molecules having a high percent (e.g., 70% or more) sequence identity to a native MCP-3 gene.

Non-naturally occurring MCP-3 gene variants are nucleic acids that do not occur in nature (e.g., are made by the hand of man), have at least 75% sequence identity with a native MCP-3 gene, and encode polypeptides having structural similarity to a native MCP-3 protein. Examples of non-naturally occurring MCP-3 gene variants are those that encode a fragment of a native MCP-3 protein, those that hybridize to a native MCP-3 gene or a complement of to a native MCP-3 gene under stringent conditions, those that share at least 65% sequence identity with a native MCP-3 gene or a complement of a native MCP-3 gene, and those that encode a MCP-3 fusion protein.

Nucleic acids encoding fragments of a native MCP-3 protein within the invention are those that encode, amino acid residues of a native MCP-3 protein. Shorter oligonucleotides that encode or hybridize with nucleic acids that encode fragments of a native MCP-3 protein can be used as probes, primers, or antisense molecules. Longer polynucleotides that encode or hybridize with nucleic acids that encode fragments of a native MCP-3 protein can also be used in various aspects of the invention. Nucleic acids encoding fragments of a MCP-3 can be made by enzymatic digestion (e.g., using a restriction enzyme) or chemical degradation of the full length native MCP-3 gene or variants thereof.

Nucleic acids that hybridize under stringent conditions to one of the foregoing nucleic acids can also be used in the invention. For example, such nucleic acids can be those that hybridize to one of the foregoing nucleic acids under low stringency conditions, moderate stringency conditions, or high stringency conditions are within the invention.

Nucleic acid molecules encoding an MCP-3 fusion protein may also be used in the invention. Such nucleic acids can be made by preparing a construct (e.g., an expression vector) that expresses an MCP-3, fusion protein when introduced into a suitable target cell. For example, such a construct can be made by ligating a first polynucleotide encoding a MCP-3 protein fused in frame with a second polynucleotide encoding another protein such that expression of the construct in a suitable expression system yields a fusion protein.

The oligonucleotides of the invention can be DNA or RNA or chimeric mixtures or derivatives or modified versions thereof, single-stranded or double-stranded. Such oligonucleotides can be modified at the base moiety, sugar moiety, or phosphate backbone, for example, to improve stability of the molecule, hybridization, etc. Oligonucleotides within the invention may additionally include other appended groups such as peptides (e.g., for targeting target cell receptors in vivo), or agents facilitating transport across the cell membrane. hybridization-triggered cleavage. To this end, the oligonucleotides may be conjugated to another molecule, e.g., a peptide, hybridization triggered cross-linking agent, transport agent, hybridization-triggered cleavage agent, etc.

The MCP-3 can be provided into or about the ischemic tissue of the mammalian subject to be treated by administering the MCP-3 to the tissue neat or in a pharmaceutical composition. The pharmaceutical composition can comprise the MCP-3 can be delivered by various methods depending on the tissue, which is to be treated. In one aspect, the pharmaceutical composition can be delivered by injection.

When administering the MCP-3 parenterally, the MCP-3 will generally be formulated in a unit dosage injectable form (e.g., solution, suspension, and/or emulsion) Examples of pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol, and the like), suitable mixtures thereof and vegetable oils.

Proper fluidity can be maintained, for example, by the use of a coating, such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the MCP-3 utilized in practicing the present invention in the required amount of the appropriate solvent with various amounts of the other ingredients, as desired.

The MCP-3 can also be provided in pharmaceutical "slow release" capsules or "sustained release" compositions or preparations, as described above. The slow release formulations are typically implanted in the vicinity of the ischemic tissue site, for example, in or about the ischemic tissue.

Alternatively, the MCP-3 can be provided in or about the ischemic tissue of the mammalian subject to be treated by introducing an agent into target cells that causes, increases, and/or upregulates expression of the MCP-3 from the target cells. The target cells can include cells within or about the periphery of the ischemic tissue or ex vivo cells that are biocompatible with the ischemic tissue being treated. The biocompatible cells can include autologous cells that are harvested from the subject being treated and/or biocompatible allogeneic or syngeneic cells, such as autologous, allogeneic, or syngeneic stem cells (e.g., mesenchymal stem cells), progenitor cells (e.g., multipotent adult progenitor cells) and/or other cells that are further differentiated and are biocompatible with the ischemic tissue being treated. Where the target cells are cells that are transplanted into the tissue to be treated, the target cell can be same cell type as the cells of the tissue being treated or a different cell type. Optionally, the target cell can comprises the same cells that are genetically modified to express SDF-1.

By way of example, where the tissue to be treated is infarcted myocardium the cells that are transplanted into the tissue to be treated can include cultured heart cells, skeletal myoblasts, fibroblasts, smooth muscle cells, and bone marrow derived cells. These cells can be harvested from the subject to be treated (i.e., autologous cells) and cultured prior to transplantation. Autologous cells are preferred to allogeneic and syngeneic cells in order to increase the biocompatibly of the cells upon transplantation and minimize the likelihood of rejection.

The cultured cells can be transplanted in the ischemic tissue by, for example, injecting a suspension of the cultured cells using a tuberculin syringe into the ischemic tissue.

The agent that is introduced into the target cells can comprise natural or synthetic nucleic acids (e.g., MCP-3 nucleic acids) that are incorporated into recombinant nucleic acid constructs, typically DNA constructs, capable of introduction into and replication in the cell. Such a construct preferably includes a replication system and sequences that are capable of transcription and translation of a polypeptide-encoding sequence in a given target cell.

Other agents can also be introduced into the target cells to cause expression of the chemokine ligands from the target cells. For example, agents that increase the transcription of a gene encoding MCP-3 increase the translation of an mRNA encoding MCP-3, and or those that decrease the degradation of an mRNA encoding MCP-3 could be used to increase MCP-3 levels. Increasing the rate of transcription from a gene within a cell can be accomplished by introducing an exogenous promoter upstream of the gene encoding MCP. Enhancer elements which facilitate expression of a heterologous gene may also be employed.

One method of introducing the agent into a target cell involves using gene therapy. Gene therapy in accordance with the present invention can be used to express the MCP-3 from a target cell in vivo or in vitro.

One method of gene therapy uses a vector including a nucleotide encoding a MCP-3. Vectors can include, for example, viral vectors (such as adenoviruses ('Ad'), adeno-associated viruses (AAV), and retroviruses), liposomes and other lipid-containing complexes, and other macromolecular complexes capable of mediating delivery of a polynucleotide to a target cell.

Vectors can also comprise other components or functionalities that further modulate gene delivery and/or gene expression, or that otherwise provide beneficial properties to the targeted cells, such as described above with respect to SDF-1.

Vectors that encode the expression of the MCP-3 can be delivered to the target cell in the form of an injectable preparation containing pharmaceutically acceptable carrier, such as saline, as necessary. Other pharmaceutical carriers, formulations and dosages can also be used in accordance with the present invention.

Where the target cell comprises a cell of the tissue to be treated, the vector can be delivered by, for example, direct injection using a tuberculin syringe under fluoroscopic guidance, at an amount sufficient for the MCP-3 to be expressed to a degree which allows for highly effective therapy. By injecting the vector directly into the tissue to be treated it is possible to target the gene rather effectively, and to minimize loss of the recombinant vectors.

This type of injection enables local transfection of a desired number of cells, in the effected tissue, thereby maximizing therapeutic efficacy of gene transfer, and minimizing the possibility of an inflammatory response to viral proteins.

Where the target cell is a cultured cell that is later transplanted into the ischemic tissue, the vectors can be delivered by direct injection into the culture medium. The MCP-3 nucleic acids transfected into cells may be operably linked to any suitable regulatory sequence, including a tissue specific promoter and enhancer.

The transfected target cells can then be transplanted to ischemic tissue by well known transplantation techniques, such as by direct injection. By first transfecting the target cells in vitro and then transplanting the transfected target cells to the ischemic tissue, the possibility of inflammatory response in the ischemic tissue is minimized compared to direct injection of the vector into the ischemic tissue.

The MCP-3 of the present invention may be expressed for any length of time within the target cell, including transient expression and stable, long-term expression. Long term expression of the MCP-3 is advantageous because it allows the concentration of stem cells to be increased at a time remote from surgery or a procedure that transplants transfected target cells. Additionally, long term or chronic up-regulation of MCP-3 would allow multiple attempts at increasing the stem cell concentration in the peripheral blood. Further, chronic up-regulation in the chemokine ligand expression causes long term homing of stem cells into the tissue to be treated from the peripheral blood without the need of stem cell mobilization agent.

In an aspect of the invention, the MCP-3 can be administered to or about the periphery of the ischemic tissue before, after, or at the substantially the same time as the administration of the SDF-1. In one aspect of the invention, where the SDF-1 and MCP-3 are administered to the ischemic tissue at substantially the same time, the SDF-1 and MCP-3 can be provided in pharmaceutical composition, which can be administered to or about the periphery of the ischemic tissue. In another aspect, where the SDF-1 and MCP-3 are expressed from a target cell in the ischemic tissue at substantially the same time, the target cell can be transfected with a bicistronic expression construct that expresses the SDF-1 and MCP-3, Bicistronic expression constructs are known in the art and can be readily employed in the present therapeutic process.

In still a further aspect of the invention, the method can include a step of increasing the concentration (i.e., number) of stem cells and/or progenitor cells, such as MSCs, MAPCs, and/or other stem cells and/or progenitor cells, in the peripheral blood from a first concentration to a second concentration substantially greater than the first concentration. The first concentration of stein cells and/or progenitor cells can be the concentration of stem cells typically found in the peripheral blood at a time remote from the onset of the ischemic disorder or tissue injury. The concentration of stem cells and/or progenitor cells in the peripheral blood can be increased while the concentration of SDF-1 and/or MCP-3 protein in or about the periphery of the ischemic tissue is increased. The concentration of stem cells and/or progenitor cells in the peripheral blood can be increased either before or after the SDF-1 and/or MCP-3 protein administration to the ischemic tissue.

The stem cells and/or progenitor cells can be provided in the peripheral blood of the tissue being treated by directly injecting the stem cells and/or progenitor cells into the tissue or tissue proximate the tissue being treated by using, for example, a tuberculin syringe. The stem cells and/or progenitor cells can also be provided in the peripheral blood by venous or arterial infusion of the stem cells into the mammalian subject to be treated. The infused stem cells and/or progenitor cells can then be induced to migrate to the tissue being treated by the SDF-1 and/or MCP-3 provided in or about the tissue.

The stem cells and/or progenitor cells can be injected or infused into the mammalian subject after providing the SDF-1 and/or MCP-3 in the tissue being treated. The stem cells and/or progenitor cells, however, can be administered before providing the SDF-1 and/or MCP-3 in the tissue being treated.

Alternatively, the stem cells and/or progenitor cells can be provided in the tissue to be treated by administering an agent to induce mobilization of stem cells, such as MSCs and/or MAPCs, to the peripheral blood of the subject. The stem cells and/or progenitor cells can be mobilized to the peripheral blood of the subject to increase stem cells and/or progenitor cells concentration in peripheral subject using a number of agents. For example, to increase the number of stem cells in the peripheral blood of a mammalian subject, an agent that causes a pluripotent stem cells and/or progenitor cells to mobilize from the bone marrow can be administered to the subject. A number of such agents are known and include cytokines, such as granulocyte-colony stimulating factor (G-CSF), granulocyte-macrophage colony stimulating factor (GM-CSF), interleukin (IL)-7, IL-3, IL-12, stem cell factor (SCF), and flt-3 ligand; chemokines such as IL-8, Mip-1α, and Groβ, and the chemotherapeutic agents of cylcophosamide (Cy) and paclitaxel. These agents differ in their time frame to achieve stem cell mobilization, the type of stem cell mobilized, and efficiency.

The mobilizing agent can be administered by direct injection of the mobilizing agent into the subject. Preferably, the mobilizing agent is administered after the SDF-1 and/or MCP-3 is provided in the ischemic tissue being treated. The mobilizing agent, however, can be administered before the SDF-1 and/or MCP-3 is administered in the tissue being treated.

EXAMPLES

The present invention is further illustrated by the following series of examples. The examples are provided for illustration and are not to be construed as limiting the scope or content of the invention in any way.

Example 1

SDF-1 Expression by Mesenchymal Stem Cells Results in Trophic Support of Cardiac Myocytes Following Myocardial Infarction The transplantation of multiple stem cell types at the time of myocardial infarction has been shown to improve left ventricular perfusion and/or function in preclinical and clinical studies. While this strategy holds great potential for the prevention and treatment of congestive heart failure, a condition that affects over 5 million Americans, the mechanisms behind the improvement remain unclear. One possibility is that the transplanted stem cells regenerate myocardial tissue by differentiating into cardiac myocytes, endothelial cells and smooth muscle cells. Another less explored possibility is that the introduction of stem cells into the myocardium at the time of acute myocardial infarction (AMI) supports the injured tissue through as yet undefined trophic effects leading to preservation of cardiac myocytes and improved cardiac function. If trophic effects of stem cells prove important in the improving cardiac tissue then we have the ability to exacerbate the effects through cell based gene therapy strategies. We have recently demonstrated that stromal cell derived factor-1 (SDF-1 or CXCL12) is expressed by the heart immediately post-MI and that re-establishment of SDF-1 expression at a time remote from MI can reestablish stem cell homing to damaged cardiac tissue. CXCR4 is the cell surface receptor for SDF-1, and is expressed on early hematopoietic stem cells (HSC) and endothelial progenitor cells. Unfortunately, emerging data indicate that these cell types do not differentiate into cardiac myocytes. While the expression of SDF-1 results in homing of HSC and endothelial progenitor cells to the injured myocardium, evidence suggests that SDF-1 can have additional non-stem cell recruiting effects including increasing stem cell survival. Recently, SDF-1 has been shown to have growth and survival benefits in CXCR4 expressing MSC. MSC normally express SDF-1; therefore, in an attempt to define the trophic effects of MSC stem cell infusion through SDF-1, we generated MSC that over-expressed SDF-1. We then compared the effects of saline, MSC and MSC that over-express SDF-1 on MSC survival, cardiac myocyte survival and regeneration, and cardiac function. Our results demonstrate a significant role for non-stem cell horning trophic effects of SDF-1 on injured myocardium.

Materials and Methods
LAD Ligation:

All animal protocols were approved by the Animal Research Committee and all animals were housed in the AAALAC animal facility of the Cleveland Clinic Foundation. Ligation of the left anterior descending artery in Lewis rat was performed as previously described. Briefly Animals were anesthetized with intraperitoneal ketamine and xylazine and intubated and ventilated with room air at 75 breaths per minute using a pressure-cycled rodent ventilator (RSP1002, Kent Scientific Corp, Torrington, Conn.). Anterior wall myocardial infarction was induced by direct ligation of the left anterior descending (LAD) artery with the aid of a surgical microscope (M500, LEICA Microsystems, Bannockburn, Ill.).

Cell Preparation and Delivery:

Rat bone marrow was isolated by flushing the femurs with 0.6 ml DMEM (GIBCO, Invitrogen, Carlsbad, Calif.). Clumps of bone marrow were gently minced with a 20 gauge needle. Cells were separated by Percoll density gradient. The cells were centrifuged for 10 minutes at 260 g and washed with three changes of PBS with 100 U/ml penicillin 100 g/ml streptomycin (Invitrogen, Carlsbad, Calif.). The washed cells were then re-suspended and plated in DMEM-LG (GIBCO, Invitrogen, Carlsbad, Calif.) with 10% FBS and 1% antibiotic and antimycotic (GIBCO, Invitrogen, Carlsbad, Calif.). The cells were incubated at 37° C. Non-adherent cells were removed by replacing the medium after 3 days. Cultures were refed every 3-4 days. When cultures became 70% confluence, adherent cells were detached following incubation with 0.05% trypsin and 2 mM EDTA (INVITROGEN, Carlsbad, Calif.) for 5 minutes and subsequently passaged. In preceding experiments, MSC Cultures were depleted of CD45+, CD34+ cells by negative selection using 10 µl each of primary PE-conjugated mouse anti-rat CD45 (BD Biosciences, San Diego, Calif.) and CD34 antibodies (Santa Cruz Biotechnology, Inc., Santa Cruz, Calif.) per 106 cells. PE-positive cells were negatively selected using the EasySep PE selection kit according to the manufacturer's instruction (Stem Cell technologies) to prevent non-specific selection of monocytes and macrophages. Confluent cells were passaged and plated out at 1:2 to 1:3 dilutions until passage 11. Cells were assayed for their ability to be induced into the adipogenic, chondrogenic, and osteogenic lineages, as described in the. Cells were maintained in differentiation media for 2 to 3 weeks. Differentiation was validated by staining the cells with Oil Red (adipogenic lineage), alcian blue (chondrogenic lineage), or alkaline phosphatase (osteogenic lineage). Two million labeled cells (cardiac fibroblasts, MSC or SDF-1 expressing MSC) harvested in 200 ml of PBS or 200 ml of PBS alone were infused via tail vein 24 hours after myocardial infarction.

BrdU Labeling:

MSC in vitro prior to cell transplantation: MSC (passage 6) were stably transfected with rat SDF-1 expression vector or pcDNA3.1 (control vector). Two days before infusion, the cells were freshly plated out at 1:3 ratio and incubated in complete medium with 10 µM BrdU (5-bromo 2-deoxyuridine) to label those cells in the S phase of the cell cycle during the 48 h period prior to harvest for cell transplantation.

Cell In Vivo After Cell Transplantation:

In those studies in which proliferating cells in vivo were labeled BrdU (50 mg kg) was injected ip every 12 hours for 14 days beginning the day after cell transplantation.

GFP Labeling of Cells:

We used a VSV-G pseudotyped lentivirus expressing EGFP or SDF-1. The lentivirus was made using four plasmid vector system by the Viral Core at the Cleveland Clinic Foundation. The MSC were be transduced twice for 8 h with purified lentivirus in the presence of 8 µg/ml of polybrene at a multiplicity of infection (MOI) of 30. The media was changed 72 h post transfection and replaced with regular media containing zeocin (EGFP) or zeocin and blasticidin (hSDF1 and EGFP). Thus, only cells that have incorporated the viral genome, including the zeocin and/or blasticidin resistance gene survived.

Real-Time PCR:

RT-PCR was performed following isolation of RNA from 6 million cells by using a Rneasy Mini Kit (Qiagen Inc., Valencia, Calif.) according to manufacturer instructions. Quantitative real-time PCR was performed by using the ABI Prism 7700 sequence detector (Applied Biosystems, Foster City, Calif.). The reaction mixture contained SYBR Green PCR master mix (Applied Biosystems, Foster City, Calif.), each primer at 300 nM, and 10 ul of cDNA. After activation of the AmpliTaq Gold (Applied Biosystems, Foster City, Calif.) for 10 minutes at 95° C., we carried out 45 cycles with each cycle consisting of 15 seconds at 95° C. followed by 1 minute at 60° C. The dissociation curve for each amplification was analyzed to confirm that there were no nonspecific PCR products.

CXCR4 Primer Sequences:

```
                                          (SEQ ID NO: 8)
    Forward: ATCATCTCCAAGCTGTCACACTCC;

(SEQ ID NO: 9)
    Reverse: GTGATGGAGATCCACTTGTGCAC
```

Immunostaining:

Animals were sacrificed 96 h or 5 w following myocardial infarction. Tissues were fixed in formalin and embedded in paraffin blocks according to established protocols. Antigen retrieval was performed using 10 mM sodium citrate buffer (pH 6.0) and heat at 95° C. for 5 minutes. The buffer was replaced with fresh buffer and re-heated for an additional 5 minutes and then cooled for approximately 20 minutes. The slides were then washed in de-ionized water three times for 2 minutes each. Specimens were then incubated with 1% normal blocking serum in PBS for 60 minutes to suppress non-specific binding of IgG. Slides were then incubated for 60 minutes with the mouse anti-BrdU primary antibody (BD Biosciences, San Jose, Calif.). Optimal antibody concentration was determined by titration. Slides were then washed with phosphate buffered saline (PBS) and then incubated for 45 minutes with FITC-conjugated secondary antibody (Santa Cruz Biotechnology Inc., Santa Cruz, Calif.) diluted to 1.5 ug/ml in PBS with serum and incubated in a dark chamber. After washing extensively with PBS, coverslips were mounted with aqueous mounting medium (Vectashield Mounting Medium with DAPI, H-1200; Vector Laboratories, Burlingame, Calif.).

Confocal Immunofluorescence Microscopy:

Tissue were analyzed using a upright spectral laser scanning confocal microscope (Model TCS-SP; Leica Microsystems, Heidelberg, Germany) equipped with blue argon (for DAPI), green argon (for Alexa Fluor 488) and red krypton (for Alexa Fluor 594) laser. Data was collected by sequential excitation to minimize "bleed-through". Image processing, analysis and the extent of colocalization was evaluated using the Leica Confocal software. Optical sectioning was averaged over four frames and the image size was set at 1024× 1024 pixels. There were no digital adjustments made to the images.

Flow Cytometric Analysis:

MSC cultures were prepared by Trypsin/EDTA digest. Wash cells twice with cold (1×) D-PBS and then resuspend cells in 1× binding buffer (10 mM HEPES, 140 mM NaCl, 2.5 mM CaCl2, pH 7.4) at a concentration of 1×106 cells/ml. Transfer 100 μL (1×105) cells to a 5 ml tube. Single-cell suspensions were then incubated with either 1 μL of Annexin V-PE-Cy5 (abcam, Cambridge, Mass.) or 5 μL Propidium Iodide (PI) (BD Biosciences, San Diego, Calif.) or isotype-matched control antibody. The cells were vortex gently and incubate at room temperature for 15 minutes in the dark. Then 400 mL of 1× binding buffer were added to each tube and the samples data were acquired by a Guava EasyCyte flowcytometer (Guava Technologies Hayward, Calif.) and analyzed with FlowJo (Tree Star, Inc., Ashland, Oreg.) flowcytometric analysis programs within one hour.

TUNEL Assay for Assessment of Apoptotic Cell Death:

TUNEL for detection of apoptotic nuclei was performed using terminal deoxynucleotidyl transferase (TdT)—mediated in situ fluorescein conjugated-dUTP nick end-labeling technique according to the manufacturer's protocol (Roche, Indianapolis. Ind.). The sections were incubated again with mouse monoclonal antibody (Chemicon International, Inc.) recognizing cardiac Ventricular myosin heavy chain α/β to specifically recognize apoptotic cardiomyocytes. The fluorescence staining was viewed with a confocal laser scanning microscope. The number of apoptotic cells was counted and expressed as percentage of total myocyte population.

Western Protocol:

Cell extracts were prepared in 4× reducing Lamellae Buffer (200mM Tris HCl (pH 6.8), 8% SDS, 0.1% Bromophenol Blue, 40% Glycerol). Sodium dodecyl sulfate (SDS) gels were prepared according to established protocols. Proteins were separated in a 10% SDS polyacrylamide gel. The blotting membrane was placed in 5% milk in 1×TBST (Tris Base-2.42 g, NaCl-8 g, 1M HCl-3.8 mL with pH to 7.5. Water-1 L, Tween 20-2 mL) for one hour and then probed with primary antibody (1:1000 in 5% Milk in 1×TBST) against phosphorylated Akt (Santa Cruz Biotechnology Inc., Santa Cruz, Calif.) followed by incubation with the peroxidase-conjugated anti-mouse secondary antibody (1:5000 in 1×TBST). Chemiluminescence (Amersham Biosciences UK Limited, Buckinghamshire, England) was used for visualization.

Antibodies Implemented in These Studies: Primary Antibodies:

Mouse anti-Myosin-Ventricular Heavy Chain alpha/beta Monoclonal antibody (Chemicon International, Inc.); Mouse monoclonal anti-alpha-sarcomeric actin IgM (Sigma); Mouse anti-troponin I monoclonal IgG2b antibody (Chemicon International, Inc.); Rabbit anti-GATA 4 polyclonal IgG antibody (Santa Cruz Biotechnology, Inc.); Goat polyclonal anti-Nkx-2.5 IgG antibody (Santa Cruz Biotechnology, Inc.); Rabbit polyclonal anti-MEF-2 IgG antibody (Santa Cruz Biotechnology, Inc.); mouse Monoclonal anti-alpha-smooth muscle actin-Cy3 conjugated antibody (Sigma); Rabbit polyclonal anti-human von willebrand factor; Rabbit anticonnexin-43 polyclonal IgG antibody (Santa Cruz Biotechnology, Inc.); Rabbit anticonnexin 45 polyclonal IgG antibody (Santa Cruz Biotechnology, Inc.); Goat Polyclonal anti-connexin-40 IgG Antibody (Santa Cruz Biotechnology, Inc.); Mouse IgG1 monoclonal anti-Akt1 antibody (Cell Signaling Technology); Mouse monoclonal anti-Phospho-Akt (ser473) IgG2b antibody (Cell Signaling Technology); Rabbit polyclonal anti-CXCR4 IgG (abcam); Rat monoclonal anti-BrdU-FITC conjugated (abcam).

Secondary Antibodies:

Goat anti-mouse IgG Alexa Fluor 488 (Molecular Probes); Goat anti-mouse IgG Alexa Fluor 594 (Molecular Probes); Donkey anti-rabbit IgG Alexa Fluor 488 (Molecular Probes); Donkey anti-rabbit IgG Alexa Fluor 594 (Molecular Probes); Goat polyclonal IgG anti-Fluorescein antibody (Molecular Probes); Donkey anti-goat IgG Alexa Fluor 488 antibody (Molecular Probes); Donkey anti-goat IgG antibody Alexa Fluor 594 (Molecular Probes); Goat anti-mouse IgM Alexa Fluor 488 (Molecular Probes).

Echocardiography:

2D-echocardiography was performed at 2 and 5 weeks following LAD ligation and MSC transplantation using a 15 MHz linear array transducer interfaced with a Sequoia C256 and GE Vision 7 as previously described (9;11). LV dimensions and wall thickness were quantified by digitally recorded 2D clips and M-mode images in a short axis view from the mid-LV just below the papillary muscles to allow for consistent measurements from the same anatomical location in different rats. The ultrasonographer was blinded to treatment group. Measurements were made by two independent blinded observers off-line using ProSolv echocardiography software. Measurements in each animal were made 6 times from 3 out of 5 randomly chosen M-mode clips recorded by an observer blinded to the treatment arm. Shortening fraction was calculated from the M-mode recordings. Shortening fraction (%)= (LVEDD−LVESD)/LVEDD×100, where LVEDD=left ventricular end diastolic dimension and LVESD=left ventricular end systolic dimension.

Statistical Analyses:

Data are presented as mean+s.d. Comparisons between groups were by unpaired Student t-test (vascular density), or by ANOVA with Bonferroni correction (echocardiographic data and cell engraftment data) for multiple comparisons where appropriate.

Results

Characterization of Engineered MSC

We generated MSC that were stably transfected with an SDF-1 expression vector driven by the CMV promoter (11). The MSC used in our studies expressed CXCR4 by RTPCR, Western blot (FIG. 1a) and immunohistochemistry (FIG. 1b). The population of stably transfected MSC used in our studies expressed 5.29±1.25 fold greater SDF-1 mRNA than MSC transfected with the control construct. Transfection with SDF-1 expression vector did not change CXCR4 expression (0.81±0.24, relative CXCR4 mRNA expression in SDF-1 and control MSC). Over a 24 h period in culture SDF-1 overexpressing MSC secreted significantly greater amounts of SDF-1 into the media than MSC transfected with control vector (FIG. 1c). No significant release of SDF-1 was observed in parallel cultures of cardiac fibroblasts. Consistent with SDF-1 inducing up-regulation of pro-survival signaling, as seen in progenitor cells, the MSC that over-expressed SDF-1 had greater phosphorylated Akt than control cells (FIG. 1d).

Effects of SDF-1 on MSC Survival During Hypoxia

Figure 2:
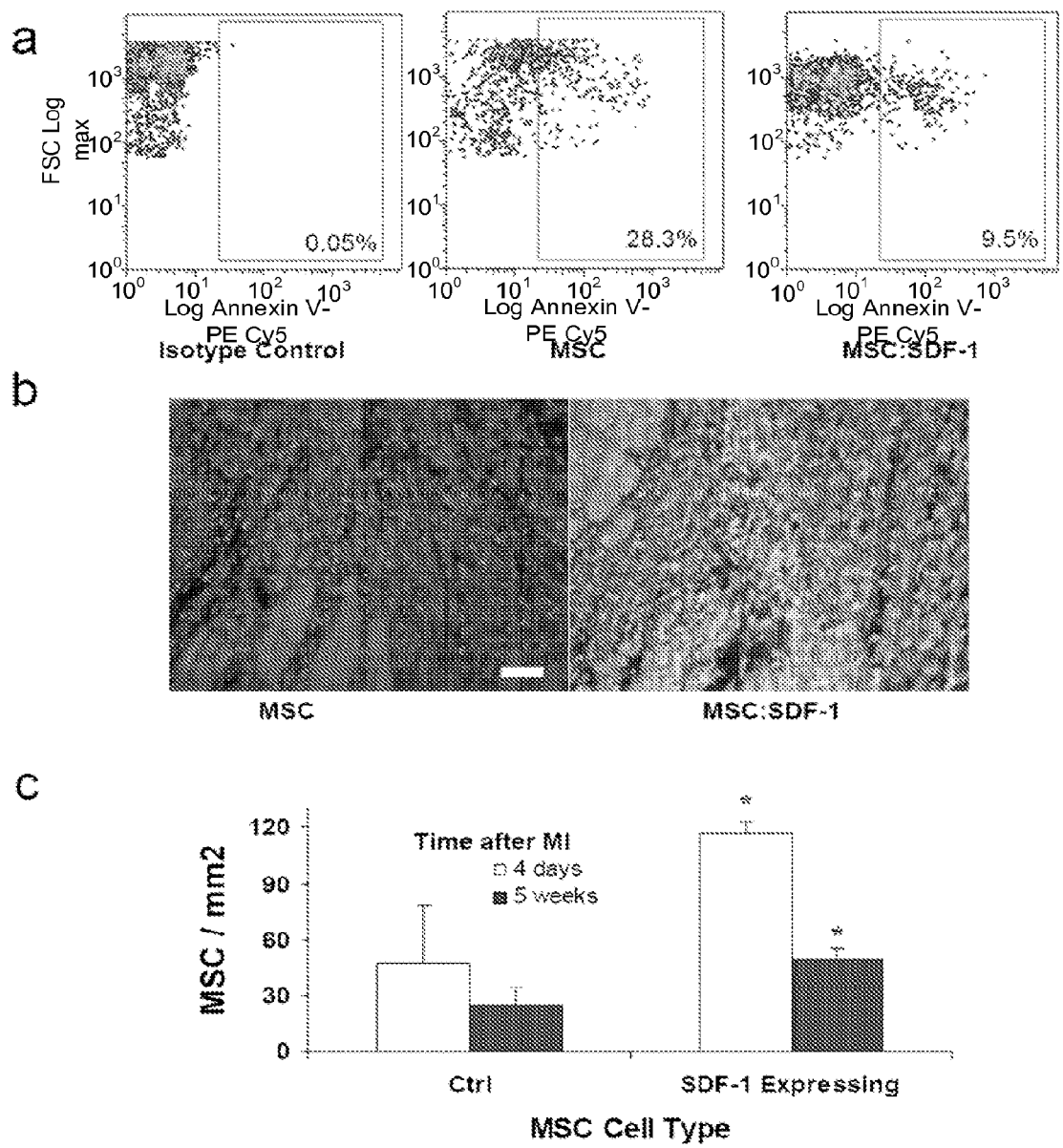
FIG. 2 illustrates a.) Representative FACS analyses for Annexin V positive cells in cultures of MSC or SDF-1 expressing cells after 72 h of being cultured under hypoxic condition (0.1% oxygen) in serum deprived culture medium (1% FBS). b.) Representative immunofluorescent staining for BrdU (FITC, Green) in the infarct zone 96 h after LAD ligation from rats that received 2 million control (left) or SDF-1 expressing MSC (right) 24 h after LAD ligation. c.) Number of MSC per square millimeter within the infarct zone at 4 d and 5 w after LAD ligation. Animals received 2 million control or SDF-1 expressing MSC 24 h after LAD ligation. MSC per square millimeter was quantified following immunofluorescent staining for BrdU. Two independent observers blinded to treatment group quantified the number of BrdU positive nuclei in the infarct zone in 10 random fields from 5 different sections (total 50 fields) obtained from the mid left ventricle. Data represent mean+SD. * represents $p<0.01$ compared to Ctrl MSC infusion.

To determine if the increase in Akt phosphorylation improved MSC survival, we cultured control and SDF-1: MSC under hypoxic conditions (1% oxygen) and quantified evidence of cell injury using FACS. The data in FIG. 2a demonstrate that >25% of MSC grown under hypoxic conditions express Annexin V compared to <10% of MSC that over-express SDF-1. Similar results were observed when the percentage of propidium iodide positive cells, a marker of cell death, was quantified (data not shown). We assessed whether similar results would be observed in vivo following myocardial infarction. Acute anterior wall myocardial infarction was induced by direct LAD ligation, twenty-four hours later, 2 million syngeneic cardiac fibroblasts stably transfected with empty plasmid, or 2 million syngeneic MSC stably transfected with empty plasmid or plasmid encoding SDF-1 were infused by tail vein injection. BrdU was added to the culture medium of the cells for 2 days prior to harvesting in order to label the cellular DNA. Control rats received an intravenous infusion of saline. Seventy-two hours and 5 weeks following treatment with cardiac fibroblasts (CF), control or SDF-1 expressing MSC or saline infusion, the animals were sacrificed and the hearts were harvested. The presence of infused CF and MSC in the heart was quantified as the number of BrdU positive cells per area. We found that the number of MSC in the heart was significantly increased by the over-expression of SDF-1 (FIG. 2b) at both time points, although the increase was significantly less at 5 weeks compared to 72 h after treatment (FIG. 2c). We did not observe evidence of significant homing or engraftment of infused cardiac fibroblasts (4 days: 3.6±2.7 cells mm$^2$ and 5 weeks: 9.9±2.1 cells mm$^2$).

Effect of SDF-1 Over-Expression on Ischemic Myocardium

FIG. 3a (24 h) shows that there is an increase in CXCR4 expression in the infarct zone as early as 24 h after AMI. These cells are not cardiac myocytes; rather, these CXCR4 positive cells are leukocytes and endothelial cells. FIG. 3a (24-48 h) demonstrates that cardiac myocytes in the infarct border zone begin to express CXCR4 as early as 48 h after AMI, and that the level of cardiac myocyte CXCR4 expression at the infarct border zone increases through 96 h after AMI. The over-expression of SDF-1 within the infarct zone via the infusion of SDF-1 expressing MSC led to an increase in the level of Akt-phosphorylation in the cardiac myocytes at the infarct border (data not shown). This increase in Akt-Phosphorylation was accompanied by a significant decrease in the number of TUNEL positive cardiac myocyte nuclei (FIGS. 3b, c and d). The decrease in cardiac myocytes apoptosis in animals that received SDF-1 expressing MSC was accompanied by a significant increase in the area of surviving bundles of cardiac myocytes within the infarct zone compared to saline controls (FIGS. 3e and f). The cardiac myocytes within the infarct zone at this time point were not BrdU positive; therefore, they were not regenerated from the engrafted MSC. Rather, they appear to be native cardiac myocytes that survived the ischemic insult.

Effects of SDF-1 Over-Expression on Cardiac Remodeling and Function

Figure 4:
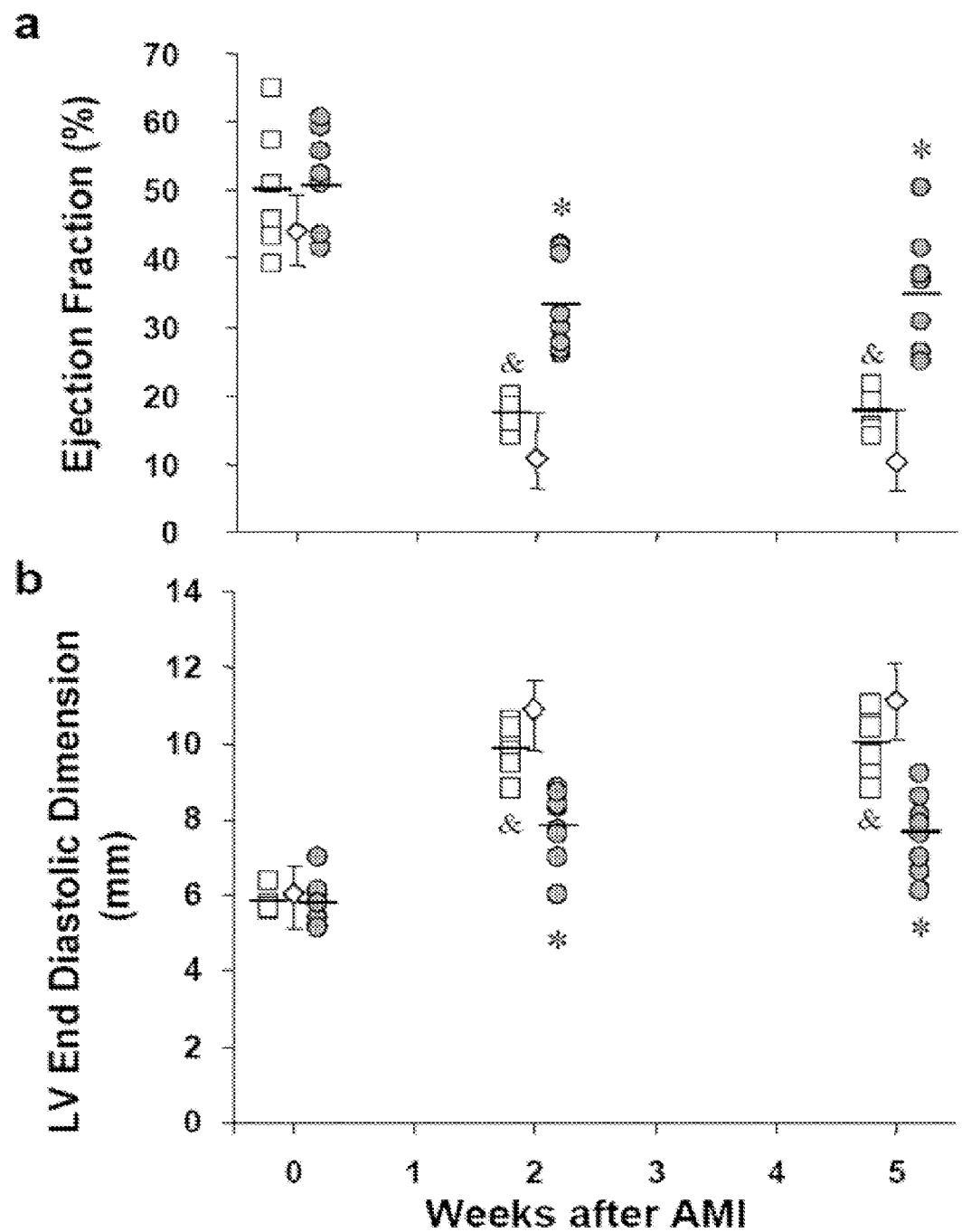
FIG. 4 illustrates a.) Cardiac function and b. Left ventricular size as quantified by the echocardiographic parameters shortening fraction and left ventricular end diastolic dimension (LVEDD), respectively. 2D and M-mode echocardiography was performed at baseline, 2 and 5 weeks after LAD ligation in animals that received saline (diamond, n=7), SDF-1 support of ischemic myocardium Thalia et al. 23 or 1 million cardiac fibroblasts (triangle, n=5), control MSC (open square, n=6) or SDF-1 over-expressing MSC (filled circle, n=8). For the animals that received saline and cardiac fibroblasts data represent mean±SD. For the animals that received MSC, individual data points are presented and the mean for that group is represented by a horizontal line. & represents $p<0.01$ and * represents $p<0.0001$ compared to Saline infusion.

We quantified left ventricular function and dimensions 14 and 35 d following LAD ligation in animals infused with saline, cardiac fibroblasts or control or SDF-1 over-expressing MSC 1 d following LAD ligation. We found a statistically significant attenuation of LV dilation and improvement in shortening fraction with MSC infusion compared to saline controls. (FIGS. 4a and b, respectively). In those animals treated with control and SDF-1 expressing MSC, shortening fraction was significantly increase by 71% and 238%, respectively, compared to saline controls. No significant difference was observed between saline infusion and cardiac fibroblast infusion.

Immunofluorescence using antibody for vWF was used to identify and quantify the vascular density within the infarct zone following each treatment. We observed a significant increase in the number of capillaries and small arterioles in those animals that received SDF-1 over-expressing MSC (18.2±4.0 vs. 7.6±2.3 vessels/mm$^2$, p<0.01). This observation is consistent with previous studies that have demonstrated that local SDF-1 expression leads to homing of endothelial progenitor cells (11;14).

Cardiac Myocytes Regeneration Verses Preservation

Figure 3:
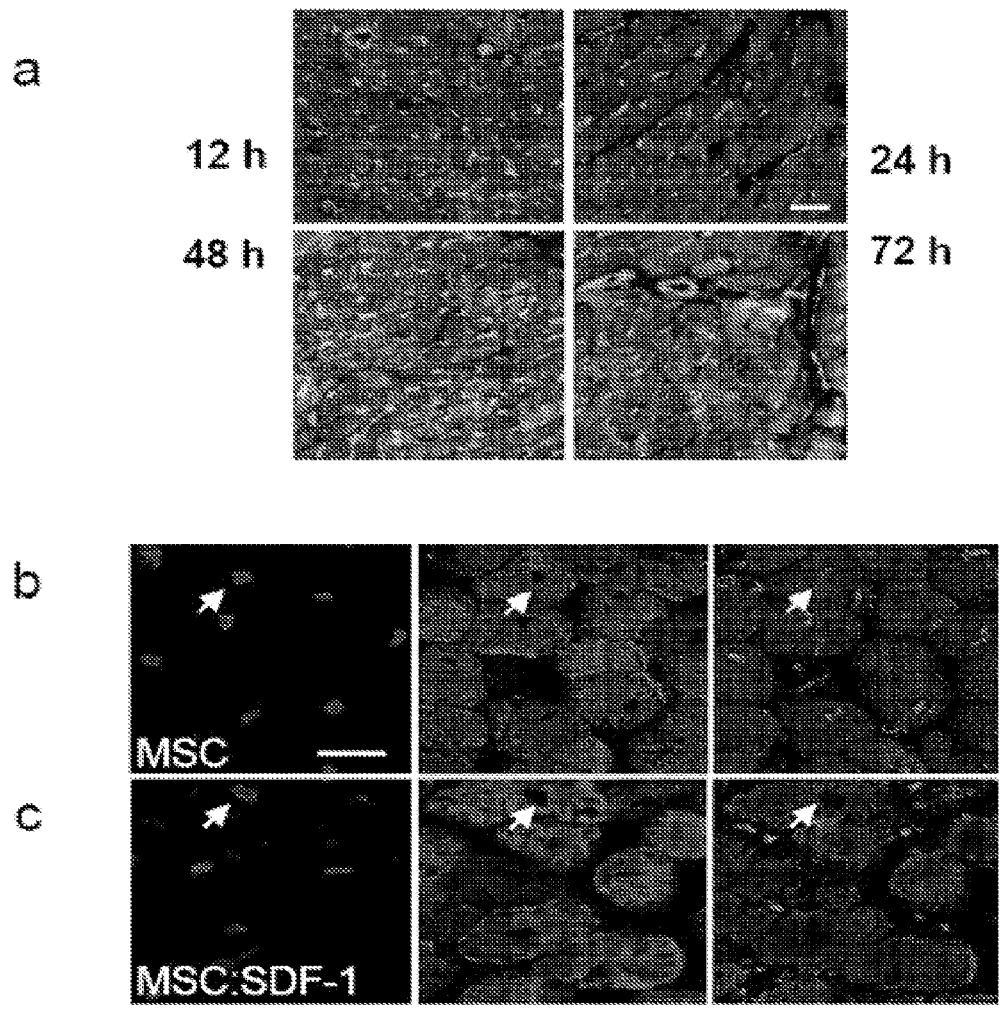
FIG. 3 illustrates a.) Confocal image of representative immunofluorescent staining for CXCR4 (Alexa Fluor 488, Green) and Troponin I (Alexa Fluor 594, Red) in the infarct border zone 12-72 h after LAD ligation. b.) and C.) Confocal image of representative immunofluorescent staining for (Left) Cardiac Myosin (Alexa Fluor 594, Red) and (Center) TUNEL (Alexa Fluor 488, Green) and (Right) merged image from an animal 96 h after LAD ligation and 72 h after infusion of b. control and c. SDF-1 expressing MSC. Arrows identify the same nuclei in each picture of a given series. d.) Number of TUNEL positive nuclei in the infarct border zone 96 h after LAD ligation in animals that received control or SDF-1 over-expressing MSC 24 h after AMI. Two independent observers blinded to treatment group quantified the number of TUNEL positive nuclei in 1000 nuclei within 4-5 cells from the infarct border zone from 5 different sections (total 5000 nuclei total) obtained from the mid left ventricle. Data represent the mean percent TUNEL positive cells±SD. * represents $p<0.0001$ compared to Ctrl MSC infusion. e.) Percent area positive for cardiac myosin within the infarct zone 5 w after LAD ligation in animals that received saline or control or SDF-1 over-expressing MSC 24 h after AMI. Percent cardiac myosin positive area was obtained by segmenting the image based on greyscale value using NIH Image by an observer blinded to treatment group. Five sections per animal were quantified. Data represent mean±SD. & represents $p<0.01$ and * represents $p<0.0001$ compared to Saline infusion. f.) Representative sections obtained 5 w after AMI stained for cardiac myosin (FITC, green) from animals that received saline, control or SDF-1 over-expressing MSC.
Figure 3:
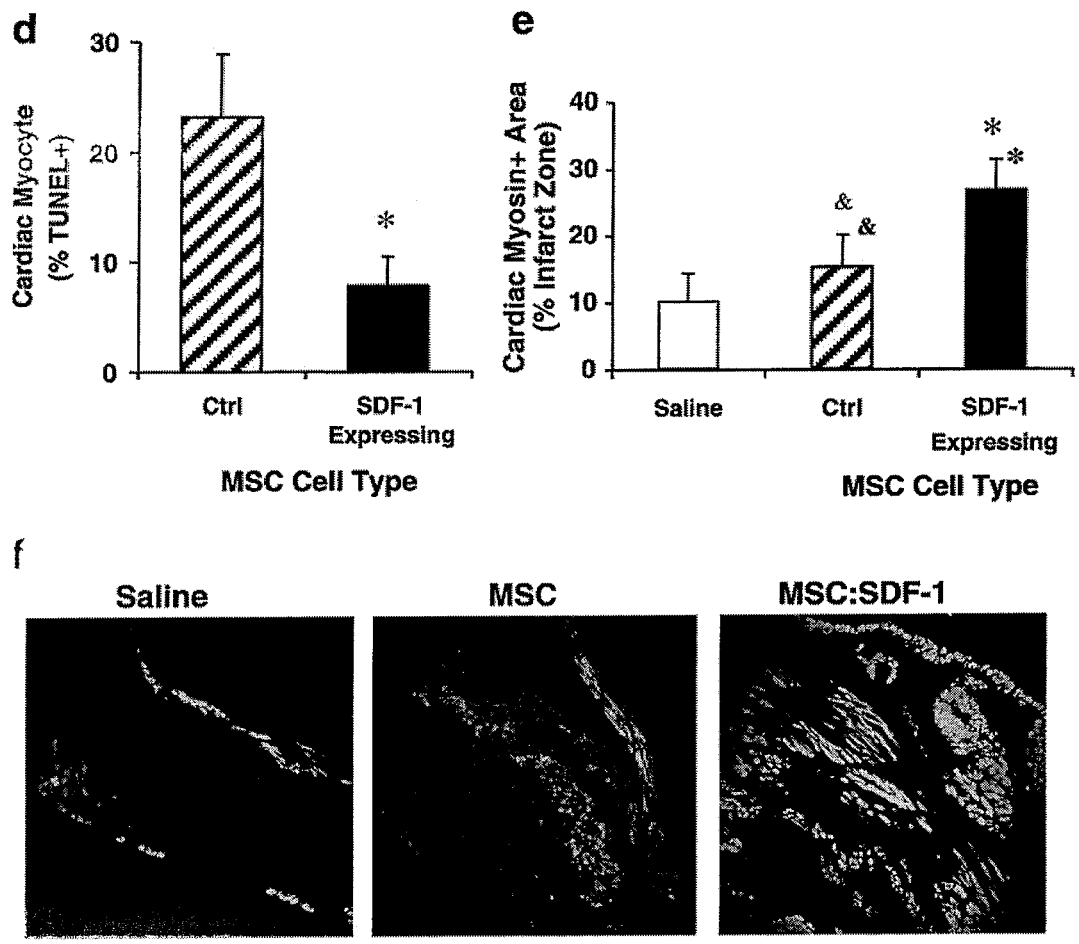
Figure 5:
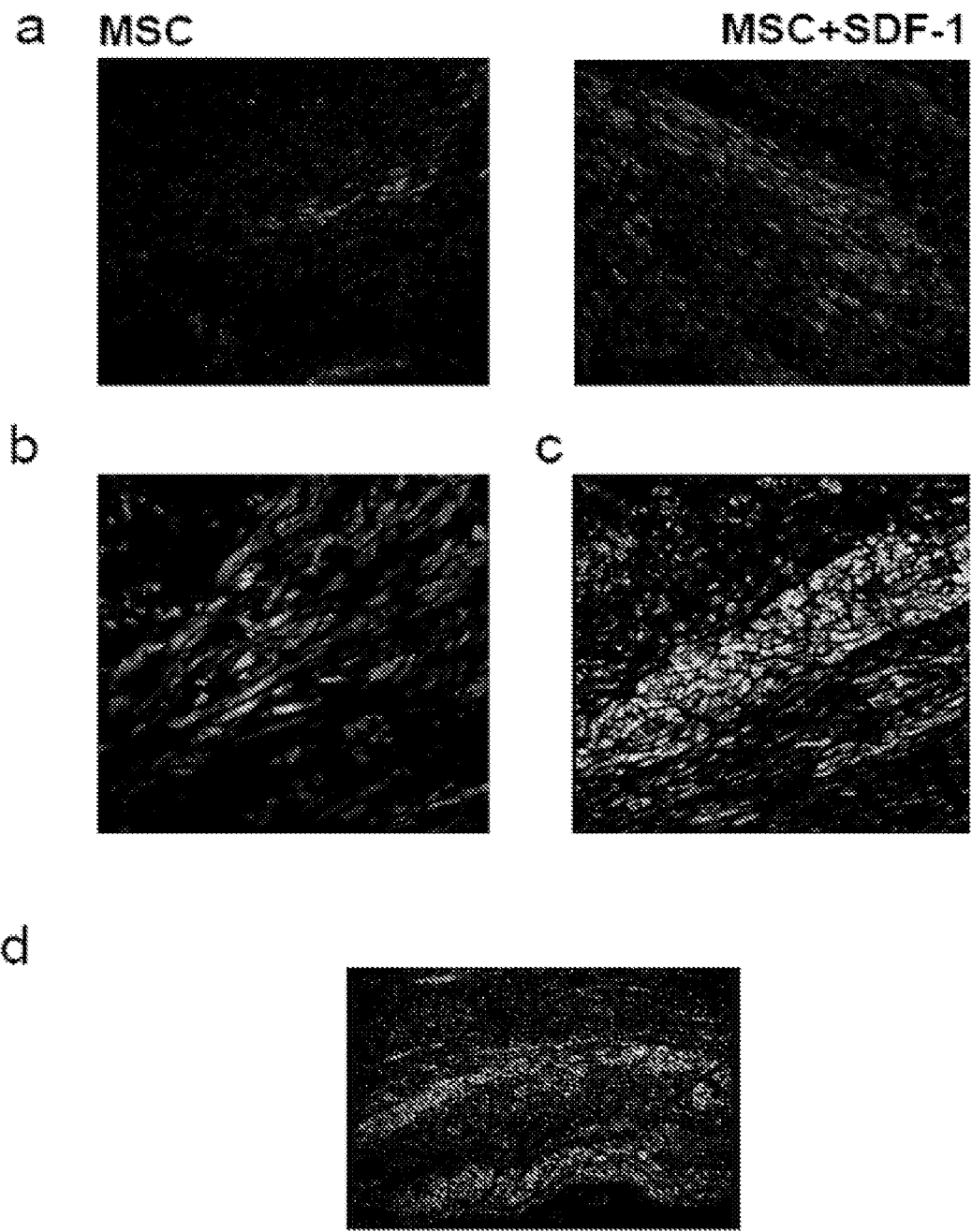
FIG. 5 illustrates representative images from tissue 5 weeks after AMI and infusion of 2 million of control or SDF-1 expressing MSC 1 day after AMI. a.) Immunofluorescent staining for smooth muscle cell α-actin (Cy3, Red) and cell nuclei (DAPI, Blue) from animals that received control (left) or SDF-1 expressing (right) MSC. b.) Confocal image of immunofluorescent staining for α-actin (Cy3, Red), cell nuclei (DAPI, Blue) and b. BrdU (FITC, Green) and c.) connexin 45 (Alexa Fluor 488, Green) front an animal that received SDF-1 expressing MSC. d.) Low power confocal image of immunofluorescent staining as in c.

The data in FIG. 3 demonstrates that MSC and to a greater extent SDF-1 expressing MSC increase the area and number of cardiac myocytes within the infarct zone. While the data in FIGS. 1-3 support the concept that this increase is due to cardiac preservation, we wanted to determine the extent to which either the injected MSC or the endogenous cardiac stem cells participated in cardiac myocyte regeneration. To determine the fate of the engrafted MSC, we stained sections of myocardial tissue for markers of cardiac myocytes (Cardiac Myosin, Troponin I, GATA4 and Connexin 43), smooth muscle cells (SMC α-actin and Connexin 45) and endothelial cells (vWF and Connexin 40). We observed that the BrdU or GFP labeled cells engrafted into the myocardium were α-actin positive (FIG. 5a). BrdU or GFP positive cells were never vWF and rarely (<2%) cardiac myosin positive suggesting that with or without SDF-1 transfection, MSC appear to either not differentiate (MSC are SMC α-actin in culture, data not shown) or differentiate into smooth muscle cells.

We also observed a significant increase in α-actin cells within the infarct zone of those animals that received SDF-1 expressing MSC that were not BrdU or GFP positive (FIG. 5b). We stained these sections for Connexin 40, 43 and 45 to determine if these cells could be electrically coupled, and thus, contribute to the improved cardiac function we observed in animals that received SDF-1 expressing MSC. We found that the α-actin cells were connexin 45 positive (FIG. 5c) and Connexin 40 and 43 negative. Of note, MSC in culture were SMC α-actin and connexin 45 positive in culture; therefore, it is unclear if the MSC in our studies differentiated at all. These α-actin and connexin 45 positive cells formed a band along the middle of the infarct zone in those animals that received SDF-1 expressing MSC, but not MSC alone (FIG. 5d).

To determine if cardiac stem cells led to the regeneration of cardiac myocytes we repeated our studies using GFP-labeled MSC and GFP-labeled SDF-1 over-expressing MSC, but in these studies we administered BrdU to the animals twice-daily beginning on the day after cell transplantation. We hypothesized that if cardiac stem cells differentiate into cardiac myocytes following LAD ligation and MSC infusion, they would proliferate prior to migration and/or differentiation. Therefore, if there were no BrdU positive cardiac myocytes we could rule out a role for cardiac stem cells in cardiac myocyte regeneration.

Figure 6:
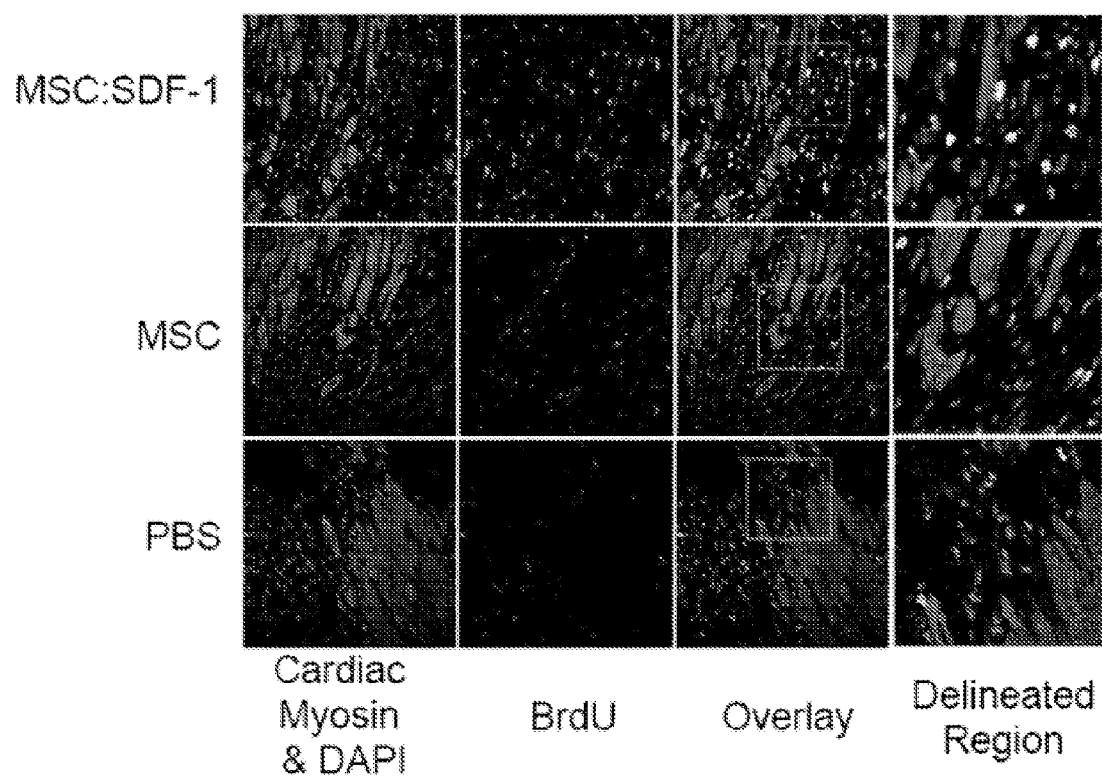
FIG. 6 illustrates representative images from tissue 5 weeks after AMI and infusion of 2 million of control or SDF-1 expressing GFP positive MSC 1 day after AMI. All animals received BrdU twice daily for 14 days beginning on the day after cell transplantation a. Confocal images of immunofluorescent staining in the infarct border zone for cardiac myosin (Red), BrdU (Green) and cell nuclei (DAPI, Blue) from animals that received PBS or control or SDF-1 expressing MSC. Column of images on the right are high power images of the delineated areas in the low power overlay images.

The data in FIG. 6 show representative images from saline, MSC and SDF-1:MSC treated animals double stained for BrdU and cardiac myosin. There is a greater number of BrdU positive cells in the SDF-1:MSC treated animals compared to MSC and saline treated animals. Interestingly, many of these BrdU positive cells in the SDF-1:MSC treated animals are cardiac myosin positive suggesting that they could be of cardiac stem cell origin; however, these BrdU and cardiac myosin positive cells are not mature cardiac myocytes. These data are consistent with the hypothesis that cardiac stem cells are mobilized by MSC alone and to a greater extent SDF-1 over-expressing MSC, they do not form mature cardiac myocytes, at least by 5 weeks after LAD ligation.

To determine if the engrafted MSC proliferated within the myocardial tissue, we double stained BrdU and GFP tissue sections from saline, MSC and SDF-1 expressing over-expressing MSC treated animals. We observed significant MSC proliferation with control and SDF-1 over-expressing MSC; however, the majority of BrdU positive cells within the tissue sections were not derived from the infused MSC (data not shown).

Discussion

The goal of stem cell based therapies following AMI is to (i) minimize myocardial cell death, (ii) optimize LV remodeling and (iii) regenerate myocardial structures, including blood vessels and cardiac myocytes. Recent studies have suggested that stem cell engraftment into recently infarcted myocardium can lead to improved cardiac function. Whether this is guided by a cache of resident cardiac stem cells that replace damaged myocardium, bone marrow-derived stem cells that home to damaged myocardium, or exogenous cells infused intravenously following MI is not fully understood.

Furthermore, the ability of hematopoietic stem cells to trans-differentiate into cardiac myocytes remains a matter of ongoing debate, however, appears unlikely given recent results. Despite this uncertainty, it is clear that the introduction of a variety of stem cell types from varied sources can lead to improved cardiac function. These findings ultimately suggest that a naturally occurring albeit clinically inefficient cardiac reparative system seems to exist at some basal level that is potentially exploitable.

Effects of SDF-1 in Post-MI Myocardial Tissue

The goal of our study was to determine the potential role SDF-1 has in the reparative process, and to determine if over-expressing SDF-1 in the peri-infarct period would lead to improvements in left ventricular function.

We chose to use MSC to deliver SDF-1 to the infarct zone because they are easy to expand in culture, may be able to differentiate into cardiac myocytes, and home to the newly infracted myocardium. We chose to use a cell therapy based approach for the delivery of SDF-1 in order to induce a sustained release of SDF-1, similar to that which may be achieved through the transplantation of stem cells in to the myocardium. Multiple recent studies suggest that some populations of MSC do express CXCR4; however, the extent to which CXCR4 expressing MSC home SDF-1 in vivo remains unclear Inhibition of SDF-1:CXCR4 binding has only been shown to partially block recruitment of these MSC to the bone marrow. Also, MSC make SDF-1 (FIG. 1a) and there is little precedent for a cell that expresses both receptor and ligand to home to that ligand. Finally, the MSC delivery strategy employed in these studies is a non-invasive way to deliver genes to the recently injured heart. CXCR4 expressing MSC do respond to SDF-1. Consistent with our data, it has recently been shown that SDF-1 leads to increased survival and growth of CXCR4 expressing MSC.

The engraftment of SDF-1 expressing MSC had multiple positive effects. Cardiac myocytes and muscle progenitor cells have previously been shown to express CXCR4. First, we found that cardiac myocytes naturally begin to express CXCR4 between 24 and 48 h after AMI (FIG. 3a). This observation suggests that delivering SDF-1 to the cell surface of injured cardiac myocytes could lead to inhibition of myocyte apoptosis as it did to MSC cultured under ischemic conditions (FIG. 2a). We observed an 80% decrease in cardiac myocytes apoptosis at the infarct border zone in those animals that received SDF-1 over-expressing MSC. This led to a significant increase in the survival of cardiac myocytes bundles within the infarct zone of those animals that received SDF-1 expressing MSC.

Second, the over-expression of SDF-1 in the infarct zone resulted in neovascularization. This is likely due to the increased recruitment of endothelial progenitor cells, as we have previously shown in a model of ischemic card iomyopathy. There was no gross pathological evidence of hemangioma formation from the sustained expression of SDF-1 over 5 weeks.

Third, the over-expression of SDF-1 in the infarct zone unexpectedly led to a marked increase in the number of smooth muscle α-actin and connexin 45 expressing cells that appear to for in a band along the middle of the infarct zone. While some of these cells are front the MSC that were infused 1 day post MI, the majority are not. Furthermore, most of these smooth muscle cells were not associated with blood vessels, as demonstrated by a void of vWF or connexin expression in the area of the SMC. While it is not clear that these cells contract in unison, it is intriguing to note that these SMC express connexin 45 and may contract in response to mechanical stretch during the cardiac cycle.

Fourth, SDF-1 in the myocardium led to recruitment and proliferation of a cardiac myosin positive cell population consistent with cardiac stem cells. While these cells did not appear to differentiate into mature cardiac myocytes within the time frame of our studies, the presence of these cells may suggest a potential for long-term benefit.

Route of Delivery

The route of cell delivery in our study was tail vein infusion. Other studies have sought to define the ideal route of cell delivery, including mobilization from bone marrow, catheter-based intra-coronary infusion, and intra-myocardial injection. Catheter based intra-coronary delivery of MSC in the left circumflex artery of dogs led to microinfarction, which may not be well tolerated in patients with little cardiac reserve. Our results highlight the fact that a simple intravenous infusion may be highly effective; while at the same time minimize mechanical risk to the freshly injured myocardium.

MSC Differentiation

Reports in the literature suggest that MSC delivered during the peri-infarct period can differentiate into cardiac myosin expressing cells. Despite being able to significantly increase MSC survival in post-MI myocardium, MSC whether labeled with BrdU or GFP did not demonstrate significant regeneration of cells with a cardiac myocyte phenotype. Thus, while it is possible that a small population of the engrafted MSC may have differentiated to a cardiac myocyte phenotype, our data are consistent with the hypothesis that the overall benefit of MSC therapy is not due to regeneration, but rather preservation of cardiac tissue and that at least one factor mediating this effect is SDF-1.

Conclusions

Our data are consistent with the concept that there is a naturally occurring regenerative repair process that occurs in infarcted myocardium that can be enhanced through the overexpression of SDF-1 within the myocardium following myocardial infarction. Interestingly, we observed multiple beneficial effects on the myocardium, apparently independent of the effects of the intravenously delivered stem cells themselves. Rather, these observed beneficial effects may be due to local paracrine effects; and could explain the improvement in cardiac function that is observed with the introduction of unfractionated bone marrow preparations in the peri-infarct period. These studies demonstrate that stem cell transplantation may have significant effects on cardiac function independent of cardiac myocyte regeneration, and that strategies designed to exploit these effects can lead to significant preservation of cardiac function. Several studies have demonstrated the utility and safety of allogeneic and autologous MSC infusion in clinical populations, thus translation of an SDF-1 based therapy for preservation of myocardial tissue to patients with acute myocardial infarction should be possible.

Example 2

MCP-3 is a Myocardial Mesenchymal Stem Cell Homing Factor

We have previously demonstrated that there is transient homing of hematopoietic stem cells (HSC) to the heart following myocardial infarction (MI). The transient nature of HSC homing is due, at least in part, to the transient expression of SDF-1. Whereas HSC seem not to transdifferentiate into cardiac tissue, MSC can acquire some properties of cardiomyocytes in vitro. Since MSC have also been shown to home to the heart early after MI, we hypothesized that there are similarly chemokine(s) temporally secreted by the myocardium that can attract MSC. The current study was to identify potential MSC homing factor(s) and to test their effect on myocardial function if stably expressed within the border zone of at a time remote from MI.

Materials and Methods

LAD Ligation:

The Animal Research Committee approved all animal protocols and all animals were housed in the AAALAC animal facility of the Cleveland Clinic Foundation. Ligation of the left anterior descending (LAD) artery in an inbred strain of rat, Lewis rat, was performed as previously described. Briefly animals were anesthetized with intraperitoneal ketamine and xylazine and intubated and ventilated with room air at 80 breaths per minute using a pressure-cycled rodent ventilator (RSP1002, Kent Scientific Corp, Torrington, Conn.). Anterior wall myocardial infarction was achieved with the aid of a surgical microscope (M500, LEICA Microsystems, Bannockburn, Ill.).

Cell Preparation and Delivery:

Rat bone marrow was isolated by flushing the femurs with 0.6 ml DMEM (GIBCO, Invitrogen, Carlsbad, Calif.). Clumps of bone marrow were gently minced with a 20-gauge needle. Cells were separated by Percoll density gradient. The cells were centrifuged for 10 minutes at 260 g and washed with three changes of PBS containing 100 U/ml penicillin/100 g/ml and streptomycin (Invitrogen, Carlsbad, Calif.). The washed cells were then re-suspended and plated in DMEM-LG (GIBCO, Invitrogen, Carlsbad, Calif.) with 10% FBS and 1% antibiotic and antimycotic (GIBCO, Invitrogen, Carlsbad, Calif.). The cells were incubated at 37° C. Non-adherent cells were removed by replacing the medium after 3 days. Fourteen days later (passage 4) cells were harvested by incubation 0.05% trypsin and 2 mM EDTA (INVITROGEN, Carlsbad, Calif.) for 5 minutes. MSC Cultures were depleted of CD45+ cells by negative selection using 10 µl each of primary PE-conjugated mouse anti-rat CD45 antibodies per 106 cells (Vendor: BD Biosciences; Cat Number: 554878). PE-positive cells were negatively selected using the EasySep PE selection kit according to the manufacturer's instruction (Stem Cell technologies). The resulting MSC (passage 6-12) were used for our studies. Three days before infusion, the cells were freshly plated out at 1:3 ratio and incubated in complete medium with 10 µM BrdU (5-bromo 2-deoxyuridine) to label those cells in the S phase of the cell cycle. BrdU labeled MSC were harvested at 106 cells/100 µl of PBS.

The status of our MSC phenotype was validated by staining the cells with Oil Red (adipogenic lineage), alcian blue (chondrogenic lineage), or alkaline phosphatase (osteogenic lineage) following culture under specific differentiation conditions. The BrdU labeling had no effect on MSC proliferation or differentiation capacity.

Syngeneic rat cardiac fibroblasts were obtained from a donor Lewis rat heart stably transfected with rat MCP-3 expression vector or pcDNA3.1 (control vector) as described previously. The expression of MCP-3 was confirmed by real-time PCR. Confluent cells were passaged and plated out at 1:2 to 1:3 dilutions until passage 11.

Gene Array Analysis:

We used a chemokine/chemokine receptor array nylon membrane array system that contained 67 distinct targets (SuperArray Bioscience Corp). One microgram of total RNA was used to make cDNA by reverse transcription using random primers. cRNA was generated and hybridization performed using company supplied protocols. Chemiluminescent signals were measured using a cooled CCD camera with a 20 sec exposure time. Each filter was used once. Three individual animals were studied at each time point. Time points studied were 1 hour and 1, 3, 7 and 10 d after LAD ligation. Control groups included no surgery and 1 hour and 7 days after sham LAD ligation in which a suture was placed but not tightened over the LAD.

Myocardial Chemokine Expression as a Function of Time After AMI:

A positive result for a specific chemokine in myocardial tissue was a 3 fold increase in expression of one experimental animal compared to all controls (Sham and no surgery) that is also at least 2 fold increased in the remaining experimental animals compared to each of the controls at that time point. Furthermore, all other time points had to be increased or no change from controls.

Identification of Differential Receptor on MSC Compared to Cardiac Fibroblasts:

Because there is less variability in expression profiles from cells in cultures compared to tissue, we increased the stringency of a positive result in arrays performed on cells in culture. In this case a significant difference in receptor expression levels was defined as a 10 fold increase in expression in MSC compared to cardiac fibroblasts. Three separate cultures of each cell type were studied. All positive results were confirmed by PCR or real-time PCR.

Real-Time PCR:

RT-PCR was performed following isolation of RNA from 6 million cells by using a Rneasy Mini Kit (Qiagen Inc., Valencia, Calif.) according to manufacturer instructions. Quantitative real-time PCR was performed using the ABI Prism 7700 sequence detector (Applied Biosystems, Foster City, Calif.). The reaction mixture contained SYBR Green PCR master mix (Applied Biosystems, Foster City, Calif.), each primer at 300 nM, and 10 ul of cDNA. After activation of the AmpliTaq Gold (Applied Biosystems, Foster City, Calif.) for 10 minutes at 95° C., we carried out 45 cycles with each cycle consisting of 15 seconds at 95° C. followed by 1 minute at 60° C. The dissociation curve for each amplification was analyzed to confirm that there were no nonspecific PCR products.

Immunostaining:

Animals were sacrificed 72 hours or 4 weeks following myocardial infarction. Tissues were fixed in formalin and embedded in paraffin blocks according to established protocols. Antigen retrieval was performed using 10 mM sodium citrate buffer (pH 6.0) and heat at 95° C. for 5 minutes. The buffer was replaced with fresh buffer and re-heated for an additional 5 minutes and then cooled for approximately 20 minutes. The slides were then washed in de-ionized water three times for 2 minutes each. Specimens were then incubated with 1% normal blocking serum in PBS for 60 minutes to suppress non-specific binding of IgG. Slides were then incubated for 60 minutes with the mouse anti-BrdU primary antibody (BD Biosciences, San Jose, Calif.). Optimal antibody concentration was determined by titration. Slides were then washed with phosphate buffered saline (PBS) and then incubated for 45 minutes with FITC-conjugated secondary antibody (Santa Cruz Biotechnology Inc., Santa Cruz, Calif.) diluted to 1.5 ug/ml in PBS with 1% serum and incubated in a dark chamber. After washing extensively with PBS, coverslips were mounted with aqueous mounting medium (Vectashield Mounting Medium with DAPI, H-1200; Vector Laboratories, Burlingame, Calif.).

Confocal Immunofluorescence Microscopy:

Tissue were analyzed using a upright spectral laser scanning confocal microscope (Model TCS-SP: Leica Microsystems, Heidelberg, Germany) equipped with blue argon (for DAPI), green argon (for Alexa Fluor 488) and red krypton (for Alexa Fluor 594) laser. Data was collected by sequential excitation to minimize "bleed-through". Image processing, analysis and the extent of co-localization were evaluated using the Leica Confocal software. Optical sectioning was averaged over four frames and the image size was set at 1024×1024 pixels. There were no digital adjustments made to the images.

Quantification of MSC Engraftment and Vascular Density:

Engrafted MSC were quantified as the number of BrdU positive cells per high power field. The number of vessels was quantified as the number of vWF positive vessels per high power field. At least 8 high power fields across the infarct zone were randomly counted by two observers blinded to the treatment of the animals. The number of cells or vessels per high power field were averaged and normalized by the calibrated area per high power field.

Echocardiography:

2D-echocardiography was performed at 2 and 5 weeks following LAD ligation and MSC transplantation using a 15 MHz linear array transducer interfaced with a Sequoia C256 and GE Vision 7 as previously described. LV dimensions and wall thickness were quantified by digitally recorded 2D clips and M-mode images in a short axis view from the mid-LV just below the papillary muscles to allow for consistent measurements from the same anatomical location in different rats. The ultrasonographer was blinded to treatment group. Measurements were made by two independent blinded observers offline using ProSolv echocardiography software. Measurements in each animal were made 6 times from 3 out of 5 randomly chosen M-mode clips recorded by an observer blinded to the treatment arm. Shortening fraction was calculated from the M-mode recordings. Shortening fraction (%)= (LVEDD−LVESD)/LVEDD×100, where LVEDD=left ventricular end diastolic dimension and LVESD=left ventricular end systolic dimension.

Determination of Collagen Content:

Paraffin sections (5 μm) of the heart tissue were prepared. Sections were stained with collagen-specific Masson-Trichrome stain and observed by light microscopy. Quantitative estimation of collagen content was performed to assess fibrillar collagen accumulation (stained blue) using Image-Pro Plus version 5.1, image analysis software. Fibrosis size was quantified by % LV area containing collagen tissue (blue). Because the hearts were 8 weeks after MI and the anterior wall had significantly thinned, was also quantified the % of the LV cavity circumference that had collagen tissue as a measure of infarct size following remodeling.

In Vitro Migration Assay:

MSCs were detached with trypsin-EDTA, counted, and resuspended in complete media. Cells (1×105 in 400 μL) were then plated onto Millicell culture inserts (8-μm pore size; Millipore, Bedford, Mass.) in a 24 well plate and allowed to adhere for overnight at 37° C. To initiate migration, DMEM containing 1% FBS (600 μL) without or with the chemoattractant factor MCP-3 (R&D Systems, Minneapolis, Minn.) was added to the lower wells (in triplicate). Cells were allowed to migrate through the insert membrane for 4 hours at 37° C. The inserts were then washed with PBS and the non-migrating cells remaining on the upper surface of the insert were removed with a cotton swab. Migrating cells were fixed with 4% PFA, stained with 0.25% crystal violet and counted using a microscope (10×). The mean number of cells (±SEM) of four randomly chosen fields was calculated for each treatment.

Statistical Analysis:

Data are presented as mean+s.d. Comparisons between groups were by unpaired Student t-test (cell engraftment, collagen content), or by ANOVA with Bonferroni correction (echocardiographic data) for multiple comparisons where appropriate.

Results

MSC Transiently Home to Injured Myocardium

Figure 7:
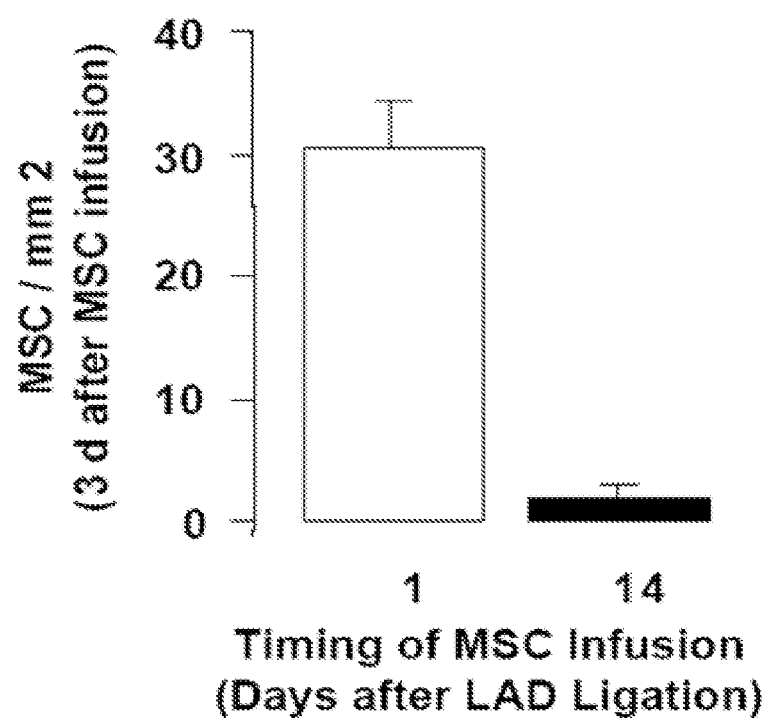
FIG. 7 illustrates MSC transiently home to the myocardium following acute MI. Two million BrdU labeled MSC were infused via the tail vein 1 d or 14 d after LAD ligation. The number of BrdU positive cells was quantified per square millimeter by immunohistochemistry 3 d after MSC infusion. Data represent mean±SD, n=5 per group.

Two million BrdU labeled MSC were infused into the tail vein of the rat at 1 or 14 d after LAD ligation. Three days following MSC infusion, the rats were killed and the heart harvested. MSC were quantified as the number of BrdU positive cells per $mm^2$. The data in FIG. 7 demonstrate that our MSC preparation transiently homes to the myocardium following acute myocardial infarction. One day after LAD ligation, a significant number of MSC was identified per unit area, where as 14 d after LAD ligation, the infusion of MSC did not result in significant MSC engraftment within the infarct zone.

Identification of Candidate MSC Homing Factors

Figure 8:
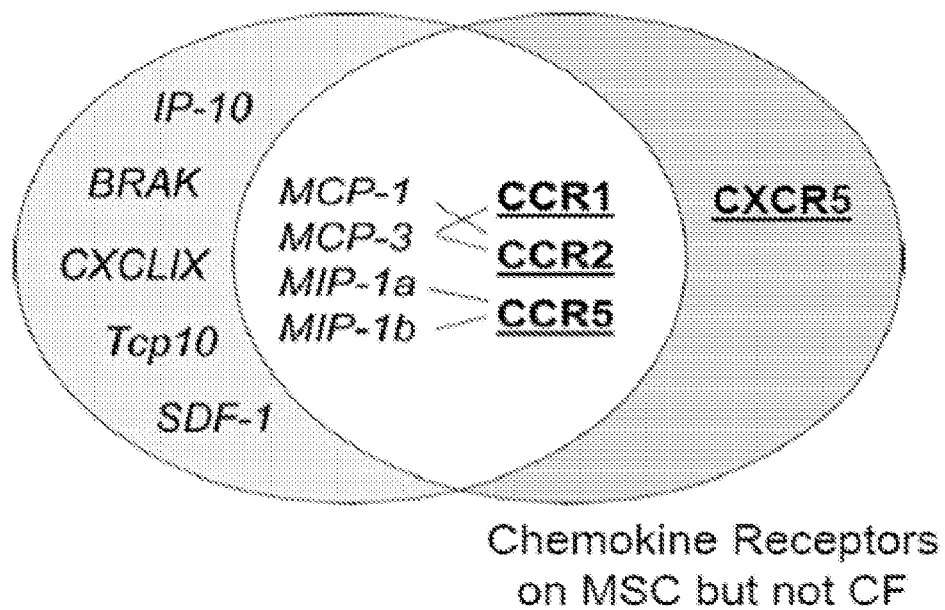
FIG. 8 illustrates MCP-3 is a candidate MSC homing factor. (a) Schematic representation of strategy and findings of array analysis identifying chemokines (Italics, Light Grey on left) expressed in the myocardium following LAD ligation and chemokine receptors (Underlined, Dark Grey Circle on right) expressed by MSC and not expressed by cardiac fibroblasts. Matched chemokine and chemokine receptors pairs of interest are delineated in the area of overlap represented by the area in the open area (b) Representative agarose gel of PCR products (40 cycles) for identified chemokine receptors in MSC at passage 6 and 20, cardiac fibroblasts and spleen (positive control). GAPDH was used as a loading control. PCR study was repeated with at least 5 samples per cell typepassage per receptor target.
Figure 8:
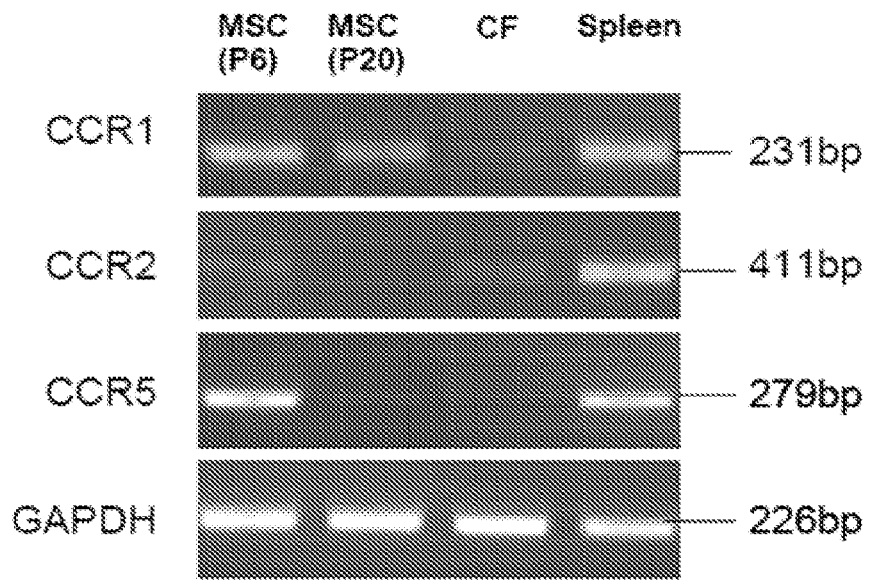

FIG. 8a depicts the strategy we implemented to identify candidate MSC homing factors. We used the chemokine and chemokine receptor array to identify two distinct lists: the first list was the population of chemokines that were expressed as early as 1 h after LAD ligation, and whose expression was gone by 10 d after LAD ligation, with a peak expression at least 3 fold over that of sham operated animals (Light Grey Grouping on Left, FIG. 8a). The second list represented chemokine receptors that were expressed at least 10 fold greater on MSC compared to cardiac fibroblasts (Dark Grey Grouping on Right, FIG. 8a). The intersection of the candidate MSC homing factors were those chemokines that were contained in the Circle on the left (Light Grey) (transiently expressed by myocardial tissue after LAD ligation) that bound receptors that were contained in the Circle on the right (Dark Grey) (expressed by MSC and not cardiac fibroblasts) are presented in the open non-shaded area. As depicted in the open area of FIG. 8a, only two families of chemokines were identified, the monocyte chemotactic proteins (1 and 3) via receptors CCR-1 and CCR-2 and MIP-1α and β via the receptor CCR-5.

In order to validate and refine the findings from our array studies, we performed PCR to further assess the presence of CCR1, CCR2 and CCR5. FIG. 8b shows PCR products from passages 6 and 20 MSC, CF and rat Spleen (positive control). These results indicate that expression of CCR1 and CCR5 are significantly greater than CF in young MSC, and that the expression of CCR5 by MSC is lost with passage.

Effect of MCP-3 Expression on MSC Homing

Based on the observation that (i) CCR1 expression appears to be maintained in MSC and (ii) the ability of MSC to home over time is not lost, we chose to focus on MCP-3. An additional pre-defined criterion for identifying an MSC homing factor is that MSC do not express the chemokine of interest. We performed real-time PCR analysis for MCP-3 expression in MSC and CF that showed MSC do not express significant levels of MCP-3 (data not shown).

Figure 9:
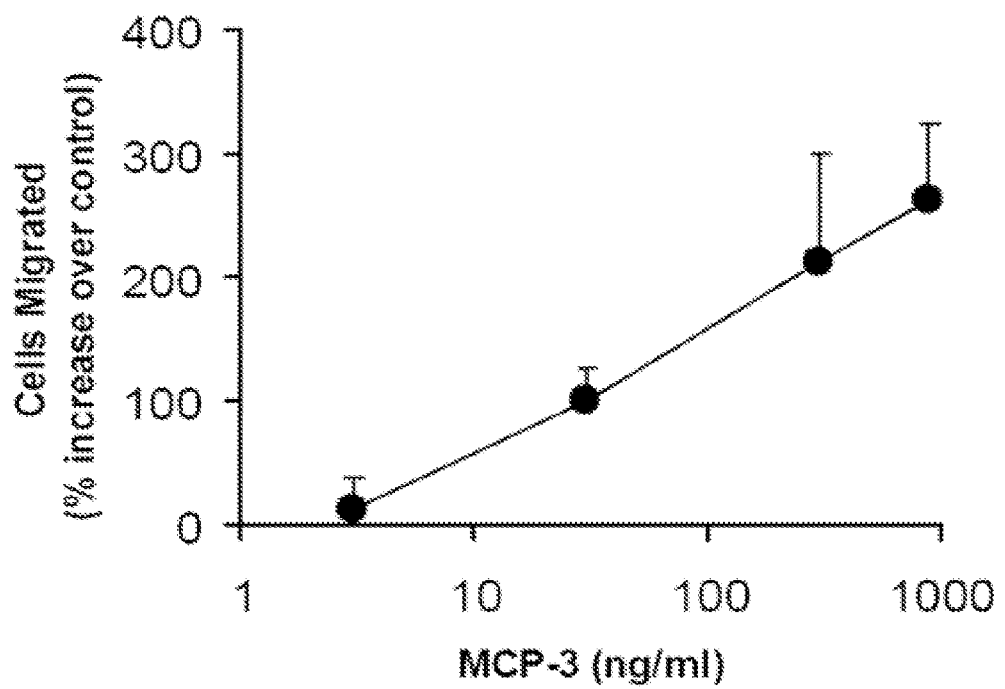
FIG. 9 illustrates MCP-3 causes MSC chemotaxis in vitro. MSC migrated in response to MCP-3 in a concentration dependent manner in an in vitro chemotaxis assay. Data represent mean±SD, n=10 per MCP-3 concentration.

To test if MCP-3 can induce MSC homing, we performed in vitro cell migration studies to test the ability of MSC to migrate in response to varying concentrations of MCP-3. The data in FIG. 9 show that there was an increase in MSC migration in a concentration dependent manner.

Figure 10:
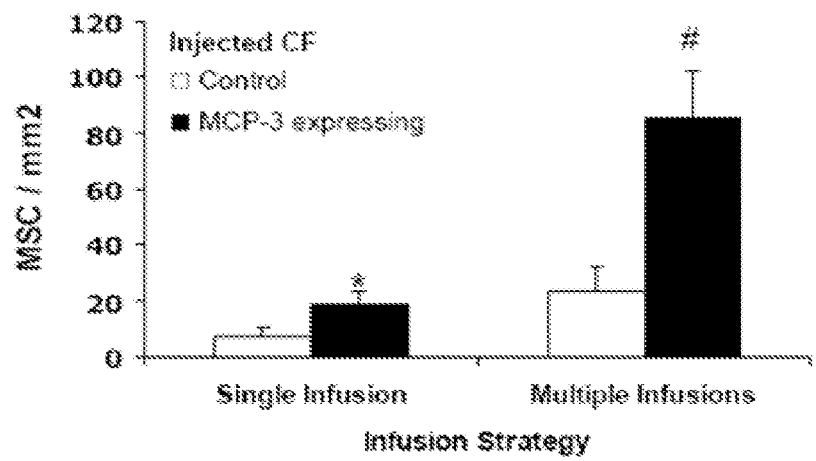
FIG. 10 illustrates MCP-3 expression leads to MSC homing to the myocardium in vivo. One month after LAD ligation 1 million control (□) or MCP-3 expressing (■) cardiac fibroblasts (CF) were transplanted into the infarct border zone. Three days later the animals received either saline, one dose (Single Infusion) or 6 doses (Multiple Infusions) 20 Schenk et al. MCP-3 and MSC horning SC-06-0293/R1 over 12 days of 1 million BrdU labeled MSC. Single Infusion animals were sacrificed 1 week after MSC infusion and Multiple Infusion animals were sacrificed 1 month after MSC infusions (10 weeks after LAD ligation). (a) The number of engrafted MSC in each treatment group was quantified per square millimeter by immunofluorescence using an antibody against BrdU. Data represent mean±SD. n=7-10 animals per group. (b) Representative photomicrographs of infarct zone following staining for BrdU (green, center images) and counterstaining for nuclei (DAPI, blue, left most images). Merged images of BrdU and nuclei are on the right. *$p<0.05$, #$p<0.001$ compared to infusion matched control cardiac fibroblast group.
Figure 10:
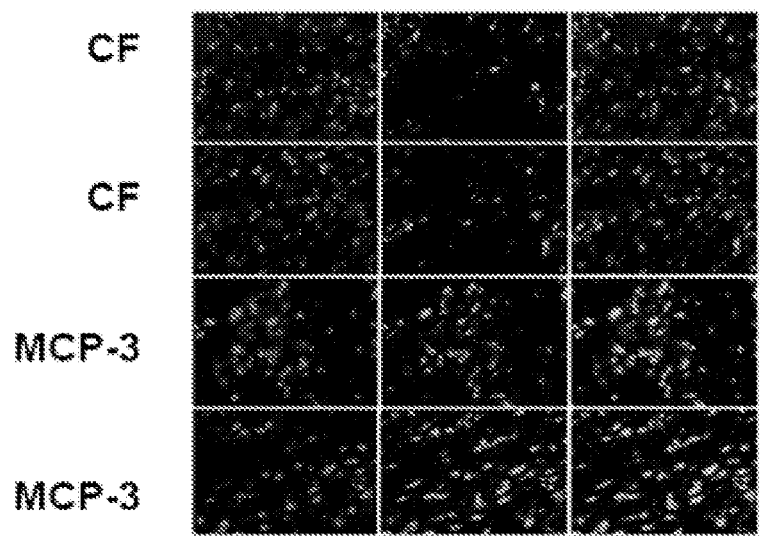

To test the ability of MCP-3 to recruit MSC to remotely injured myocardium, 1 months after LAD ligation we transplanted control or MCP-3 expressing CF into the infarct border zone. Three days later, we infused 1 million BrdU labeled MSC via the tail vein, and quantified MSC engraftment 3 days later (6 days after CF transplantation). The data in FIG. 10 (single infusion) demonstrate that re-establishment of MCP-3 expression in myocardial tissue restores the ability of MSC to home to myocardial tissue. While these data are consistent with MCP-3 having a role in MSC homing, the level of MSC engraftment was low compared to HSC engraftment in response to chronic SDF-1 expression in the same model.

We reasoned that among the causes of the relatively low engraftment of MSC in response to MCP-3 was the fact that, unlike HSC, MSC are not constitutively released by the bone marrow, some MSC are trapped in the lung when given i.v., and that the half-life of MSC in the blood stream following intravenous infusion is short (<1 h). We hypothesized that serial infusions of MSC into animals transplanted with MCP-3 expressing CF would lead to greater MSC engraftment. The data in FIG. 4 (multiple infusions) show that following 6 intravenous infusions over 12 days of 1 million MSC per infusion there were significantly greater MSC engrafted in the myocardium of animals that received MCP-3 expressing CF compared to control CF (FIGS. 10a and b).

Effect of Re-Establishing MSC Horning on Cardiac Function

Figure 11:
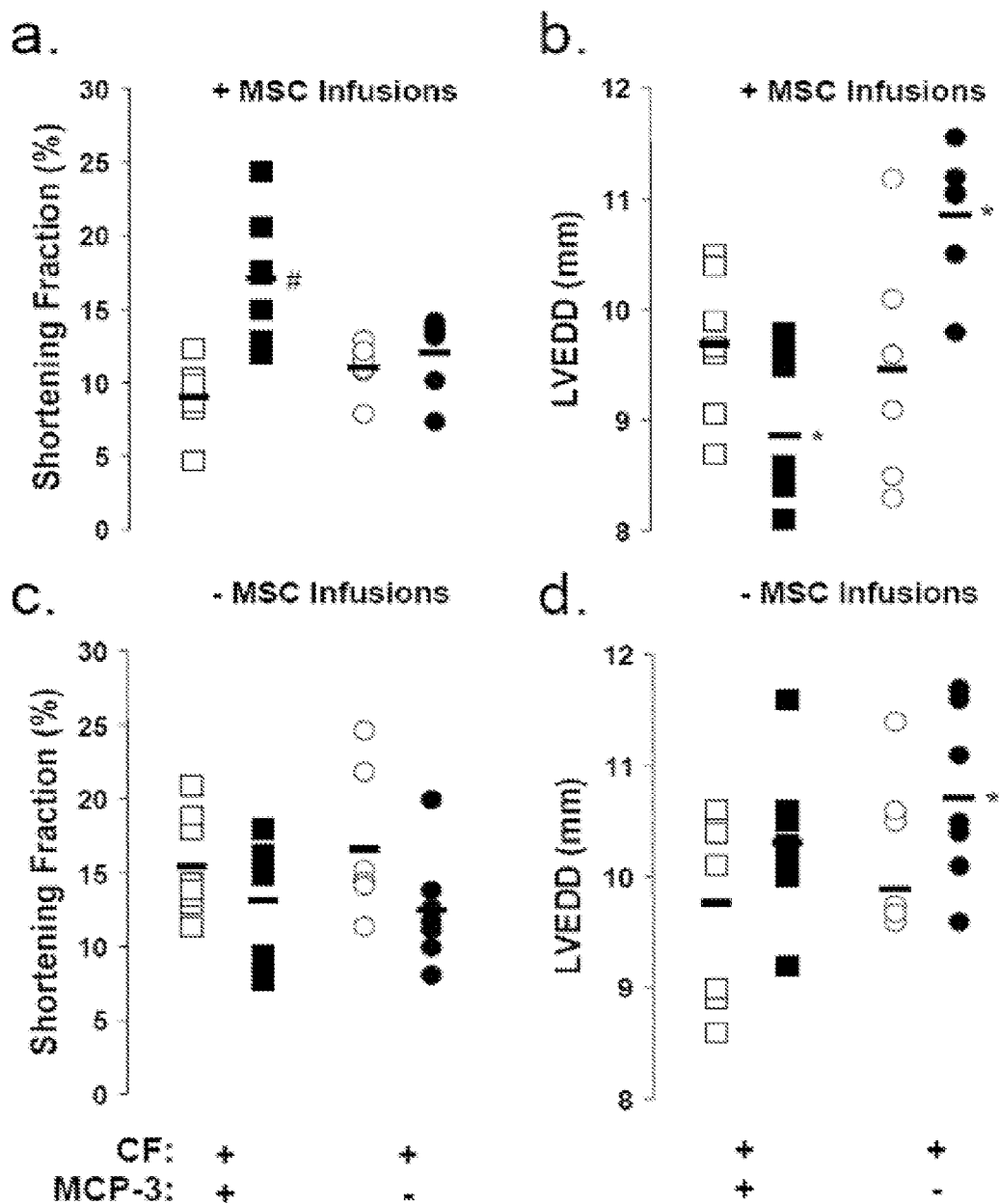
FIG. 11 illustrates MCP-3 expression combined with MSC infusions results in improved cardiac function and remodeling. One month after LAD ligation cardiac function (Shortening Fraction (%), a, c) and left ventricular end diastolic dimension (LVEDD, b, d) were quantified by echocardiography (○, □). After echocardiography 1 million control (●) or MCP-3 expressing cardiac fibroblasts (■) were transplanted into the infarct border zone. Beginning three days after cardiac fibroblast injections the animals received the first dose of 6 doses of 1 million BrdU labeled MSC (a, b) or saline (c, d). Successive doses were given every other day over the ensuing 12 days. Echocardiography was repeated 6 weeks after cardiac fibroblast transplantation (10 weeks after LAD ligation, ●, ■). Data represent individual animals. Solid lines represent the mean for the group. n=7-10 per group. *$p<0.05$, #$p<0.001$ compared to baseline parameter measured at 1 month post after myocardial infarction.

We transplanted control and MCP-3 expressing CF 1 month after LAD ligation. Following CF transplantation animals then received 6 infusions of 1 million MSC per infusion every other day for 12 days or saline beginning 3 days after CF transplantation. Cardiac function and dimensions were quantified by echocardiography 1 month after MI before CF transplantation (baseline), and 1 month after CF transplantation (2 months after MI). The data in FIG. 11a demonstrate that cardiac function as measured by shortening fraction was significantly increased in those animals that received MCP-3 expressing CF and MSC infusions. No significant benefit was seen when animals received MCP-3 expressing CF without MSC infusions (FIG. 11c). There was evidence of reverse remodeling with a decrease in LVEDD 1 month after infusion of MSC into animals that received MCP-3 expressing CF and MSC infusions. Further dilation of the left ventricular cavity was observed in those animals that received either control CF despite serial infusions of MSC or MCP-3 expressing CF without serial infusions of MSC (FIGS. 11b and d).

Figure 12:
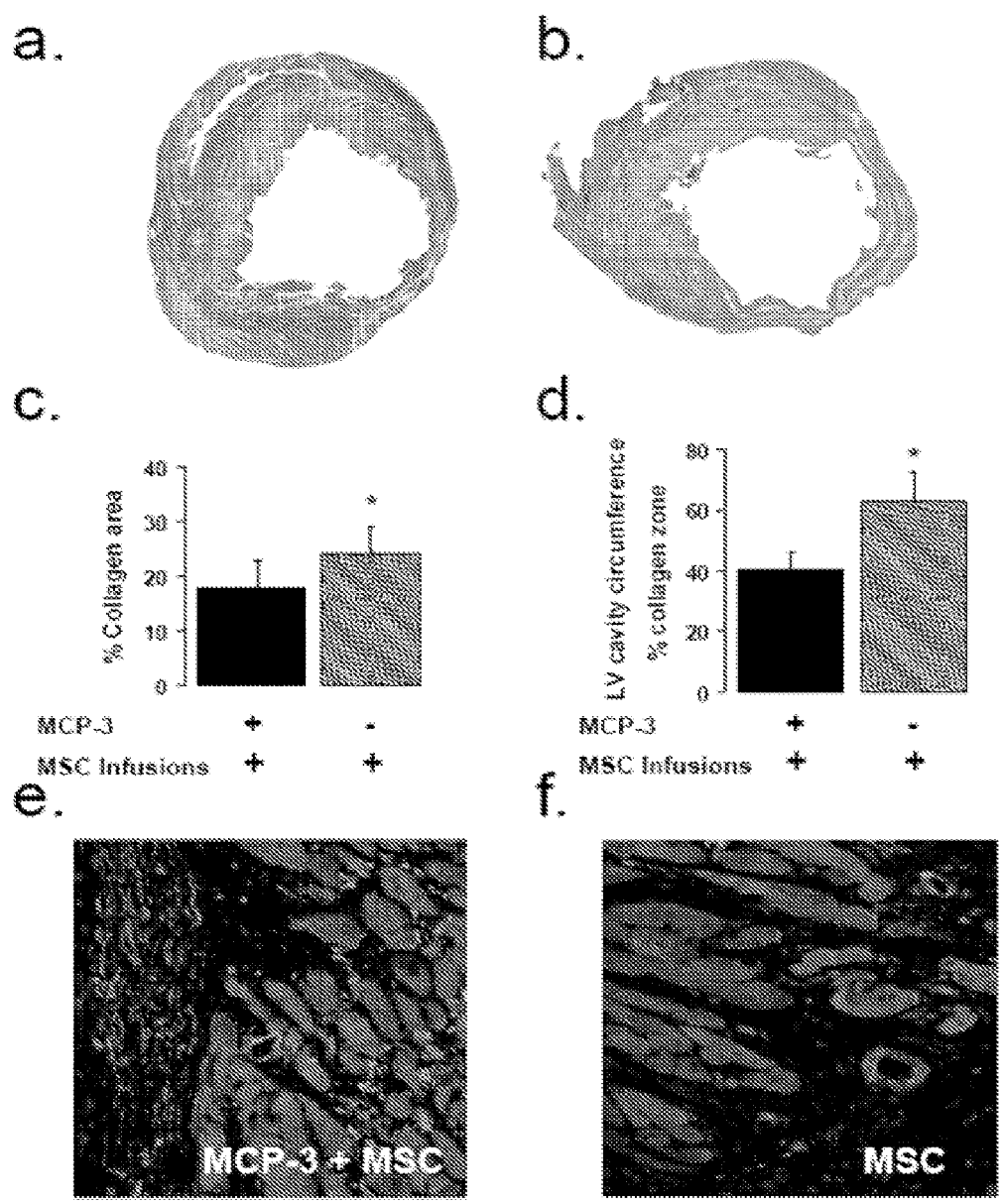
FIG. 12 illustrates MCP-expression combined with MSC infusions causes ventricular remodeling and myofibroblasts recruitment. Representative photomicrographs of 21 Schenk et al. MCP-3 and MSC homing SC-06-0293/R1 Masson trichrome stained cross sections of the mid-ventricular segments from animals the received (a) MCP-3 expressing or (b) control cardiac fibroblasts 4 weeks after LAD ligation followed by serial infusions of MSC. The (c) percent area the ventricle containing collagen fibriles or (d) the percent of the endocardial circumference in which there was collagen fibriles was quantified in 5 animals per group. Data represent mean±SD, n=5 per group *$p<0.05$. Representative confocal micrographs of myofibroblasts in the infarct border zone in animals that received serial infusions of MSC following transplantation of (e) MCP-3 expressing or (f) control cardiac fibroblasts. Tissue was stained 10 weeks after LAD ligation using immunofluorescence with an antibody that recognizes vimentin (green). The nuclei were counterstained with DAPI (blue) and the cardiac myocytes were identified using an antibody that recognizes ventricular myosin heavy chain (red).

The engrafted MSC did not differentiate into cardiac myocytes. Co-staining for BrdU and cardiac myosin, troponin I or connexin 43 revealed that none of the engrafted MSC expressed cardiac markers in vivo (data not shown). We hypothesized that MSC engraftment resulted in remodeling of the infarct zone leading to improvement in cardiac function. Mason's trichrome staining revealed a significant difference in collagen content in the infarct/infarct border zone between animals that were treated with control and MCP-3 expressing cardiac fibroblast prior to serial MSC infusion (FIGS. 12a and b, respectively). No changes were observed with the injection of MCP-3 expressing cardiac fibroblasts without MSC infusion (data not shown). Injection of CF with our without MCP-3 expression and with or without MSC infusions had no effect on vascular density (data not shown). The percent of the LV that stained positive for collagen was significantly decreased by 25.4% (p<0.02, FIG. 12c) in the animals that received MCP-3 expressing cardiac fibroblasts and serial MSC infusions. In these animals we observed a 35.3% (p<0.01, FIG. 12d) decrease in the LV circumference that stained positive for collagen. These data are consistent with our observation that there was a significant decrease in LVEDD (FIG. 11) in animals that received MCP-3 expressing cardiac fibroblasts and serial MSC infusions. Myofibroblasts have been associated with improved cardiac remodeling and function; therefore, we wanted to determine if the favorable collagen remodeling was associated with a greater number of myofibroblasts in the infarct zone. Staining with an antibody to vimentin and α-smooth muscle cell actin demonstrated a greater number of myofibroblasts in the infarct border zone of animals that received MCP-3 and serial MSC infusions compared to those that received control CF and serial MSC infusions (FIGS. 12e and f). The vimentin+ cells were rarely BrdU positive, suggesting that the majority of these cells were recruited to the infarct border zone in response to MSC engraftment since MCP-3 expression alone did not result in an increase in myofibroblasts.

Discussion

MSC are under active investigation as a stem cell source for tissue repair. MSC are known to home to injured tissue of multiple organs; however, the biological signals responsible for MSC homing have not been previously described. In this study we identified MCP-3 as a homing factor for MSC.

Some studies have suggested that MSC home in response to SDF-1. Moreover, SDF-1 seems important for growth and survival of MSC, perhaps due to autocrine mechanisms, since MSC themselves express SDF-1, but these effects of SDF-1 are distinct from SDF-1 being responsible for MSC homing. Consistent with the idea that SDF-1 over-expression at a time remote from MI does not induce significant homing of MSC, we only encountered HSC recruitment and engraftment in previous studies that defined SDF-1 as a myocardial stem cell homing factor.

MCP-3 belongs to the family of CC chemokines with potent chemotactic activities for several cell types, including monocytes, leukocytes, and dendritic cells. These chemokines exert their effects through interaction with the chemokine receptors CCR1, CCR2, CCR3, and CCR5. MCP-3 has been shown to be expressed at multiple sites of inflammation, although its role in wound healing has not been fully elucidated. In this study, we show that MCP-3 is transiently expressed by myocardial tissue following acute myocardial infarction. Since MSC are not known to be mobilized in response to myocardial infarction, the utility of MCP-3 expression as a MSC homing factor for the intrinsic repair of the heart at the time of MI is unclear. However, as shown by our study exploiting the MSC homing effects of MCP-3 may have therapeutic potential.

Our data demonstrate that following myocardial infarction there is a transient up-regulation and release of multiple chemokines that may impact on stem cell trafficking to sites of injury. Identification and re-expression of these stem cell homing factors weeks to months after myocardial infarction appears to re-establish the ability of stem cells to traffic to and engraft in the infarct zone. Furthermore, injecting the heart with cells that re-establish stem cell homing in the myocardial tissue could be a potential strategy for increasing stem cell content in the heart overtime. Future studies are necessary to determine if this strategy is equally or more efficacious as either multiple invasive injections over time and/or what can be achieved with a single injection of stem cells.

The recruitment of MSC to the heart one month after myocardial infarction did not result in regeneration of cardiac myocytes. Rather, as has been shown with MSC injections in the peri-infarct period, MSC engraftment results in beneficial remodeling in the infarct zone. The lack of new cardiac myocyte formation could be due to the inability of MSC to differentiate into cardiac myocytes or the lack of critical mediators of cell signaling required for cardiac differentiation being present in the myocardial tissue beyond the peri-infarct period. MSC are known to release multiple factors including VEGF, SDF-1, FGF, and IGF-1. While beyond the scope of our current study demonstrating that MCP-3 is an MSC homing factor, it is interesting to note that we observed improved cardiac function in the absence of vasculogenesis or angiogenesis. Thus the effects of recruiting MSC via the over-expression of MCP-3 appears distinct from that observed following over-expression of an HSC homing factor or injection of HSC themselves. This observation suggests that the mechanism of benefit following re-establishment of MSC homing and engraftment of MSC at a time remote from myocardial infarction for MSC transplantation at a time remote from acute myocardial infarction is related to improved cardiac remodeling, and perhaps trophic effects on surviving myocardium; rather than improved tissue perfusion.

From the above description of the invention, those skilled in the art will perceive improvements, changes and modifications. Such improvements, changes and modifications within the skill of the art are intended to be covered by the appended claims Additionally, all references, publications, and patent applications, and patents referred to in this application are herein incorporated by reference in their entirety.

What is claimed:

1. A method of treating ischemic cardiomyopathy in a patient in need thereof comprising administering mesenchymal stem cells that have been transfected with an expression vector that includes a nucleic acid that encodes SDF-1 protein operably linked to a promoter, by intravenous infusion, or directly to the patient's ischemic myocardium or about the periphery of said ischemic myocardium, wherein expression of the vector results in one or more of a decrease in cardiac myocyte apoptosis, neovascularization, an increase in smooth muscle α-actin- and connexin 45-expressing cells, and recruitment and proliferation of cardiac myosin positive cells.

2. The method of claim 1, wherein said method results in an increase in the concentration of SDF-1 protein in said ischemic myocardial tissue.

3. The method of claim 2, wherein said increase in the concentration of SDF-1 protein in said ischemic myocardial tissue induces stem cells to home to the ischemic myocardial tissue.

4. The method of claim 1, wherein said ischemic cardiomyopathy is the result of a myocardial infarction.

5. The method of claim 4, wherein said cells are administered at a time remote from the onset of the myocardial infarction.

6. The method of any one of the preceding claims, wherein the transfected cells have been cultured ex vivo.

* * * * *

SEQUENCE LISTING

<160> NUMBER OF SEQ ID NOS: 9

<210> SEQ ID NO 1
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Lys Pro Val Ser Leu Leu Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 2
<211> LENGTH: 89
<212> TYPE: PRT
<213> ORGANISM: Homo sapiens

<400> SEQUENCE: 2

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 3
<211> LENGTH: 89
<212> TYPE: PRT
<213> ORGANISM: Rattus norvegicus

<400> SEQUENCE: 3

Met Asp Ala Lys Val Val Ala Val Leu Ala Leu Val Leu Ala Ala Leu
1               5                   10                  15

Cys Ile Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Ser Asn Asn Arg Gln Val Cys Ile Asp Pro Lys Leu Lys Trp Ile Gln
65                  70                  75                  80

Glu Tyr Leu Asp Lys Ala Leu Asn Lys
                85

<210> SEQ ID NO 4
<211> LENGTH: 1940
<212> TYPE: DNA
<213> ORGANISM: Homo sapiens

<400> SEQUENCE: 4
gccgcacttt cactctccgt cagccgcatt gcccgctcgg cgtccggccc ccgacccgcg      60
ctcgtccgcc cgcccgcccg cccgcccgcg ccatgaacgc caaggtcgtg gtcgtgctgg     120
tcctcgtgct gaccgcgctc tgcctcagcg acgggaagcc cgtcagcctg agctacagat     180
gcccatgccg attcttcgaa agccatgttg ccagagccaa cgtcaagcat ctcaaaattc     240
tcaacactcc aaactgtgcc ttcagattg tagcccggct gaagaacaac aacagacaag     300
tgtgcattga cccgaagcta agtggattc aggagtacct ggagaaagct ttaaacaagt     360
aagcacaaca gccaaaaagg actttccgct agacccactc gaggaaaact aaaaccttgt     420
gagagatgaa agggcaaaga cgtggggag ggggccttaa ccatgaggac caggtgtgtg     480
tgtggggtgg gcacattgat ctgggatcgg gcctgaggtt tgccagcatt tagaccctgc     540

```
atttatagca tacggtatga tattgcagct tatattcatc catgccctgt acctgtgcac      600
gttggaactt ttattactgg ggttttcta agaaagaaat tgtattatca acagcatttt      660
caagcagtta gttccttcat gatcatcaca atcatcatca ttctcattct cattttttaa      720
atcaacgagt acttcaagat ctgaatttgg cttgtttgga gcatctcctc tgctcccctg      780
gggagtctgg gcacagtcag gtggtggctt aacagggagc tggaaaaagt gtcctttctt      840
cagacactga ggctcccgca gcagcgcccc tcccaagagg aaggcctctg tggcactcag      900
ataccgactg gggctgggcg ccgccactgc cttcacctcc tctttcaacc tcagtgattg      960
gctctgtggg ctccatgtag aagccactat tactgggact gtgctcagag accccctctcc    1020 cagctattcc tactctctcc ccgactccga gagcatgctt aatcttgctt ctgcttctca     1080
tttctgtagc ctgatcagcg ccgcaccagc cgggaagagg gtgattgctg ggctcgtgc      1140 cctgcatccc tctcctccca gggcctgccc cacagctcgg gccctctgtg agatccgtct     1200
ttggcctcct ccagaatgga gctggccctc tcctggggat gtgtaatggt ccccctgctt    1260
acccgcaaaa gacaagtctt tacagaatca atgcaattt taaatctgag agctcgcttt     1320
gagtgactgg gttttgtgat tgcctctgaa gcctatgtat gccatggagg cactaacaaa   1380
ctctgaggtt tccgaaatca gaagcgaaaa atcagtgaa taaaccatca tcttgccact    1440
accccctcct gaagccacag cagggtttca ggttccaatc agaactgttg gcaaggtgac   1500
atttccatgc ataaatgcga tccacagaag gtcctggtgg tatttgtaac tttttgcaag  1560 gcatttttt atatatattt ttgtgcacat ttttttttac gtttctttag aaaacaaatg    1620
tatttcaaaa tatatttata gtcgaacaat tcatatattt gaagtggagc catatgaatg   1680
tcagtagttt atacttctct attatctcaa actactggca atttgtaaag aaatatatat   1740
gatatataaa tgtgattgca gcttttcaat gttagccaca gtgtattttt tcacttgtac   1800
taaaattgta tcaaatgtga cattatatgc actagcaata aaatgctaat tgtttcatgg   1860
tataaacgtc ctactgtatg tgggaattta tttacctgaa ataaaattca ttagttgtta   1920
gtgatggagc ttaaaaaaaa                                                1940
```

```
<210> SEQ ID NO 5
<211> LENGTH: 293
<212> TYPE: DNA
<213> ORGANISM: Rattus norvegicus

<400> SEQUENCE: 5
ccatggacgc caaggtcgtc gctgtgctgg ccctggtgct ggccgcgctc tgcatcagtg       60
acggtaagcc agtcagcctg agctacagat gcccctgccg attctttgag agccatgtcg      120
ccagagccaa cgtcaaacat ctgaaaatcc tcaacactcc aaactgtgcc ttcagattg       180 ttgcaaggct gaaaagcaac aacagacaag tgtgcattga cccgaaatta agtggatcc       240 aagagtacct ggacaaagcc ttaaacaagt aagcacaaca gcccaaagga ctt            293
```

```
<210> SEQ ID NO 6
<211> LENGTH: 99
<212> TYPE: PRT
<213> ORGANISM: Homo sapiens

<400> SEQUENCE: 6

Met Lys Ala Ser Ala Ala Leu Leu Cys Leu Leu Leu Thr Ala Ala Ala
1               5                   10                  15

Phe Ser Pro Gln Gly Leu Ala Gln Pro Val Gly Ile Asn Thr Ser Thr
            20                  25                  30
```

-continued

```
Thr Cys Cys Tyr Arg Phe Ile Asn Lys Lys Ile Pro Lys Gln Arg Leu
        35                  40                  45
Glu Ser Tyr Arg Arg Thr Thr Ser Ser His Cys Pro Arg Glu Ala Val
 50                  55                  60
Ile Phe Lys Thr Lys Leu Asp Lys Glu Ile Cys Ala Asp Pro Thr Gln
 65                  70                  75                  80
Lys Trp Val Gln Asp Phe Met Lys His Leu Asp Lys Lys Thr Gln Thr
                 85                  90                  95
Pro Lys Leu
```

<210> SEQ ID NO 7
<211> LENGTH: 810
<212> TYPE: DNA
<213> ORGANISM: Homo sapiens

<400> SEQUENCE: 7

```
agcagagggg ctgagaccaa accagaaacc tccaattctc atgtggaagc ccatgccctc      60
accctccaac atgaaagcct ctgcagcact tctgtgtctg ctgctcacag cagctgcttt     120
cagcccccag gggcttgctc agccagttgg gattaatact tcaactacct gctgctacag     180
atttatcaat aagaaaatcc ctaagcagag gctggagagc tacagaagga ccaccagtag     240
ccactgtccc cgggaagctg taatcttcaa gaccaaactg acaaggaga tctgtgctga      300
ccccacacag aagtgggtcc aggactttat gaagcacctg acaagaaaa cccaaactcc      360
aaagctttga acattcatga ctgaactaaa acaagccat gacttgagaa acaaataatt      420
tgtataccct gtcctttctc agagtggttc tgagattatt ttaatctaat tctaaggaat     480
atgagcttta tgtaataatg tgaatcatgg ttttcttag tagattttaa aagttattaa      540
tattttaatt taatcttcca tggattttgg tgggttttga acataaagcc ttggatgtat     600
atgtcatctc agtgctgtaa aaactgtggg atgctcctcc cttctctacc tcatgggggt     660
attgtataag tccttgcaag aatcagtgca aagatttgct ttaattgtta agatatgatg     720
tccctatgga agcatattgt tattatataa ttacatattt gcatatgtat gactcccaaa     780
ttttcacata aaatagattt ttgtaaaaaa                                      810
```

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
atcatctcca agctgtcaca ctcc                                            24
```

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
gtgatggaga tccacttgtg cac                                             23
```